United States Patent [19]

Tompa et al.

[11] Patent Number: 5,199,970
[45] Date of Patent: Apr. 6, 1993

[54] HERBICIDAL, OPTICALLY ACTIVE OR RACEMIC SUBSTITUTED PROPIONIC ACID DERIVATIVES, HERBICIDE COMPOSITIONS CONTAINING THEM AND A PROCESS FOR PREPARING SAME

[75] Inventors: József Tompa; Ferenc Bartha; Tibor Timár; Ágota Répási née Veres; Vilmos Galamb, all of Tiszavasvári; Éva Füzi née Porkoláb, Tiszalök; Dezsó Miklós, Veszprém, all of Hungary

[73] Assignee: Alkaloida Vegyeszeti Gyar, Tiszavasvari, Hungary

[21] Appl. No.: 605,829

[22] Filed: Oct. 30, 1990

[30] Foreign Application Priority Data

Nov. 2, 1989 [HU] Hungary .................. 5645/89

[51] Int. Cl.⁵ .................. A01N 43/84; C07D 413/12
[52] U.S. Cl. .................. 504/225; 540/597; 544/131; 544/360; 546/193; 546/275; 546/281; 546/283; 546/300; 504/219; 504/235; 504/249; 504/251; 504/252; 504/257; 504/259; 504/248
[58] Field of Search ............... 546/300, 193, 275, 281, 546/283; 71/94; 544/360, 131; 540/597

[56] References Cited

U.S. PATENT DOCUMENTS

| | | | |
|---|---|---|---|
| 4,325,729 | 4/1982 | Rempfler et al. | 546/300 |
| 4,523,013 | 6/1985 | Johnson et al. | 546/300 |
| 4,555,575 | 11/1985 | Cartwright | 546/300 |

OTHER PUBLICATIONS

Nishiyama et al. "Chemical Abstracts", vol. 92, 1980, col. 92:71056h.
Nishiyama, et al. (II), "Chemical Abstracts", vol. 92, 1980, col. 92:128733h.
"Chemical Abstracts", vol. 93, 1980, col. 93:168132p.
Aya, et al., "Chemical Abstracts", vol. 102, 1985, col. 102:24498u.
Bartha, et al., "Chemical Abstracts", vol. 112, 1990, col. 112:17758g.

*Primary Examiner*—C. Warren Ivy
*Assistant Examiner*—James H. Turnipseed
*Attorney, Agent, or Firm*—Herbert Dubno; Jonathan Myers

[57] ABSTRACT

The invention relates to novel, herbicidally active 2-[4-(5-trifluoromethyl-2-pyridyloxy)phenoxy]-propionic acid derivatives of the general formula (I),

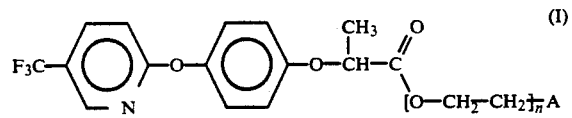

The invention also relates to herbicide compositions containing the compounds of the general formula (I) as active ingredients as well as to a process for the preparation of these compounds and compositions.

4 Claims, No Drawings

HERBICIDAL, OPTICALLY ACTIVE OR RACEMIC SUBSTITUTED PROPIONIC ACID DERIVATIVES, HERBICIDE COMPOSITIONS CONTAINING THEM AND A PROCESS FOR PREPARING SAME

FIELD OF THE INVENTION

The invention relates to novel, herbicidally active 2-[4-(5-trifluormethyl-2-pyridyloxy)phenoxy]propionic acid derivatives of the formula (I),

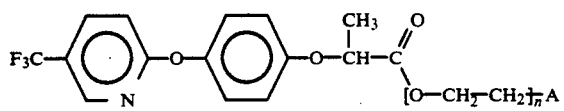

wherein
A depends on the value of n in such a way that:
1) when n is 0 (zero), A is an —$NR^1R^2$ substituted amino group, wherein
  a) $R^1$ is hydrogen; $R^2$ is a $C_{1-4}$alkyl, $C_{2-4}$alkenyl, $C_{4-7}$cycloalkyl, heteroaryl-$C_{1-4}$alkyl group or a —B—$NR^3R^4$ group, where B is a straight or branched chain $C_{2-4}$ alkylene group; $R^3$ and $R^4$ are $C_{1-4}$alkyl groups or $R^3$ and $R^4$ together form an alicyclic group containing 2 to 6 methylene groups and the cycle, when consisting of 6 members, may contain an oxygen or an additional substituted or unsubstituted nitrogen in 4-position related to the nitrogen;
  b) $R^1$ and $R^2$ are different from hydrogen and represent a $C_{1-4}$alkyl or $C_{2-4}$alkenyl group; or $R^1$ and $R^2$ together form an alicyclic group containing 2-6 methylene groups and the ring, when consisting of 6 members, may contain an oxygen in 4-position related to the nitrogen;
2) when n is other than 0 (zero) (n is 1 or 2), A is:
  a) an —$NR^5R^6$ disubstitued amino group, wherein $R^5$ and $R^6$ represent a $C_{1-4}$alkyl or $C_{2-4}$alkenyl group; or $R^5$ and $R^6$ together form an alicyclic group containing 2 to 6 methylene groups, and the ring, when consisting of 6 members, may contain an oxygen or an additional substituted or unsubstituted nitrogen in 4-position related to the nitrogen, the alicyclic ring optionally being substituted by one or more methyl groups;
  b) or an —O—N=$C(CH_3)_2$ group, in racemic or optically active form or in the form of a mixture containing the enantiomers in any ratio, as well as herbicide compositions containing these compounds or their mixture as active ingredients.

The invention further relates to the preparation of the above compounds of formula (I) and compositions containing these compounds as active ingredients.

The invention further relates to the preparation of the above compounds of formula (I) and compositions containing these compounds as active ingredients.

BACKGROUND OF THE INVENTION

A large number of novel, herbicidally active compounds have been prepared in the past years, which could be used pre-emergence and/or post-emergence.

The derivatives of 2-(heteroaryloxy-phenoxy)propionic acid are of great importance due to their high-grade selectivity, whereby they can be used with a highdegree safety for killing (controlling) annual and perennial monocotyledonous weeds in dicotyledonous cultures.

These compounds possess a relatively high translocation ability in the plant; they induce necrosis or chlorosis in the tissues of the meristem and developing leaves of sensitive plants. Via an accompanying biochemical effect, they increase the membrane-permeability and inhibit the auxin-induced reactions (hypoauxinosis). Their inhibitory effect on the de novo fatty acid biosynthesis bears the same importance in their activity as their auxin deficiency-inducing effect [Walker et al.: Biochem. J. 254, 811 (1988)].

DESCRIPTION OF THE INVENTION

The compounds of the invention possess environment-saving properties because they have a satisfactory effect even when used in relatively low doses. It has been proved by a number of experiments that there exists a significant difference between the post-emergent activity of the optical isomers; thus, by using the more active, pure enantiomer the desired effect can be achieved with lower doses and with a lower environmental pollution than those induced by the racemates or mixtures of enantiomers with various ratios.

The properties of the above compounds can be considered to be advantageous also from a toxicological point of view because they can be classified to the medium or moderately toxic substances.

Several possibilities are available for the preparation of the compounds of formula (I) according to the invention.

According to a commonly useful method the suitable heteroaryloxy-phenoxypropionyl chloride is reacted with a primary or secondary amine, alcohol or N,N-disubstituted amino-alkanol at 0°-25° C. in an inert solvent, in the presence of an acid binding agent to obtain the desired product. Examples of using this method have been described inter alia in the published German patent applications Nos. 2,755,536 (Ciba-Geigy) and 3,246,847 (Hoggo Chemical Industry Co., Ltd.), in the published European patent applications Nos. 0,120,393 (Nihon Tokushu Noyaku Seizo KK.) and 0,138,359 (the Dow Chemical Company) and in the U.S. Pat. No. 4,642,338 (the Dow Chemical Company) as well as in: G. K. Tseng et al. [J. Org. Chem. 38, 1746 (1973)]; G. Thuillier and P. Rumpf (Bull. Soc. Chim. France 1960, 1786); and J. Jandke and G. Spiteller (Liebigs Ann. Chem. 1988, 1057).

Alternatively, the desired products can be obtained by reacting various secondary amides or ester derivatives of propionic acid substituted in 2-position by halogen (chlorine or bromine), mesyloxy or tosyloxy group, with a suitable 4-heteroaryloxy-phenol usually in a polar aprotic solvent, mostly by using anhydrous potassium carbonate as acid binding agent. Examples of the use of this method have been described in the published European patent application No. 0,120,393 (Nissan Chemical Industries Ltd.) and in the published German patent application Nos. 3,004,770 (Nissan Chemical Industries Ltd.) and 3,246,847.

One variant of the above process comprises first reacting various secondary amides or ester derivatives of propionic acid substituted in 2-position by halogen, mesyloxy or tosyloxy group with hydroquinone or the monoalkyl ether thereof and then treating the 2-(4-hydroxyphenoxy)propionic acid thus obtained or after desalkylation with a suitable heteroaromatic halogen compound in a polar aprotic solvent, usually in the presence of potassium carbonate as acid binding agent to obtain the desired product.

Other methods, which are useful for the synthesis of amine-terminal esters and amides or their hydrochlorides and are different from those mentioned above, are found in the paper of G. Thuillier and P. Rumpf cited above. On reacting various aryloxyacetic acids with N,N-disubstituted aminoalkyl halides in anhydrous isopropanol at the boiling point of the reaction mixture, the corresponding hydrochlorides can be obtained from which the basic ester can be set free.

According to another example the reaction of an aryloxyacetic acid methyl ester with an asymmetrically N,N-disubstituted alkylenediamine leads to the corresponding basic amide.

The 2-[4-(5-trifluoromethyl-2-pyridyloxy)phenoxy]-propionic acid or its methyl ester used as starting materials can be prepared by several methods.

One of the suitable methods comprises reacting 4-(5-trifluoromethyl-2-pyridyloxy)phenol or its alkaline metal salt with a propionic acid or alkaline metal salt or alkyl ester thereof substituted in 2-position by halogen (chlorine or bromine), mesyloxy or tosyloxy group.

Alternatively, 2-chloro-5-trifluoromethylpyridine is brought into reaction with 2-(4-hydroxyphenoxy)propionic acid or an alkaline metal salt or alkyl ester thereof. Depending thereon if the desired product is the free acid or its methyl ester, the ester is subjected to alkaline hydrolysis or the acid is esterified in the traditional manner with methanol (e.g. by using p-toluenesulfonic acid or sulfuric acid as catalyst). Examples of the use of this method have been reported inter alia in the published German patent applications Nos. 2,755,536, 2,812,571 and 3,219,789 as well as in the published European patent application No. 0,002,925 and in the published Hungarian patent application No. 189,891.

By using optically active 2-substituted propionic acid or a suitable derivative thereof as starting material (containing one of the enantiomers in pure form or in a ratio being different from 1:1) or inactive (racemic) 2-substituted propionic acid or a suitable derivative thereof, respectively, optically active or racemic products, respectively, can be obtained.

One further possibility for preparing optically active 2-[4-(5-trifluoromethyl-2-pyridyloxy)phenoxy]-propionic acid or 2-(4-hydroxyphenoxy)propionic acid, respectively, comprises resolving a racemic acid or an acid containing the enantiomers in a ratio being different from 1:1 (prepared by using any of the methods discussed above). Suitable resolving agent for this purpose may be e.g. (R)-(+)- or (S)-(−)-1-phenylethylamine. This process has been described in the published European patent application No. 0,002,925 (Imperial Chemical Industry Ltd). 2-[4-(5-Trifluoromethyl-2-pyridyloxy)phenoxy]propionyl chloride may usually be prepared by reacting the acid with thionyl chloride. According to a variant of this process, the acid is directly heated with a relatively high excess (in a molar ratio of 1:5 to 1:6) of thionyl chloride at 60° C., optionally at the boiling point of the mixture and after termination of the reaction the excess thionyl chloride is removed, preferably under reduced pressure and nitrogen atmosphere (see the published German patent application No. 2,755,536 or the published European patent application No. 0,205,821). The modified variant differs from the above one therein that the acid is treated with a relatively low excess (in a molar ratio of 1:1.2 to 1:1.5) of thionyl chloride in an inert solvent, optionally in the presence of a catalytic amount of dimethylformamide the boiling point of the reaction mixture, then after evaporating the solution the remaining acid chloride is directly used for a further transformation. Examples of this process variant have been described in the published German patent application No. 3,219,789 and in the published European patent application No. 0,148,119.

Most of N,N-disubstituted aminoalkanols, aminoalkyl halides and alkylenediamines required for preparing the propionic acid derivatives according to the invention are well-known, available substances or they can optionally be prepared on the basis of literature references [Hartman: Org. Synth. Coll. Vol. II. pages 183–184; Moffet: Org. Synth. Coll. Vol. IV. pages 466–467; A. Funke, G. Benoit: Bull. Soc. Chim. France 20, 1021 (1953); Reppe et al.: Liebigs Ann. Chem. 596, 148 (1955); as well as Amundsen et al.: Org. Synth. Coll. Vol. III. pages 254–258].

According to the invention the compounds formula (I) defined above can be prepared by condensing a propionic acid derivative of the formula (II),

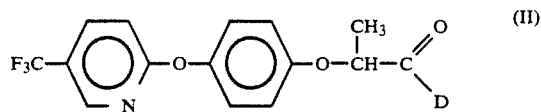

wherein D stands for chlorine or a methoxy group, with a compound of the formula (III),

wherein A and n are as defined above.

A restricted class of compounds of the formula (I), wherein A is as defined above and n is 1, can also be prepared by condensing a propionic acid of the formula (II), wherein D means hydroxyl group, with an N,N-disubstituted aminoalkyl halide of the formula (IV)

wherein B, R³ and R⁴ are as defined above.

According to one of the process variants a methyl ester of the formula (II), wherein D stands for a methoxy group, is reacted with a primary amine of the formula (V),

wherein R² is as defined above, in a molar ratio of 1:2 to 1:10, preferably in a molar ratio of 1:2 to 1:3 at 60°–150° C., preferably at 70°–80° C. This reaction is suitably carried out without any additional diluent.

According to another process variant an acid chloride of the formula (II), wherein D means chlorine, is reacted with a compound of the formula (III), wherein A and n are as defined above. This reaction is preferably performed in an anhydrous, water-immiscible inert solvent (such as toluene, chloroform, methylene chloride, 1,2-dichloroethane etc.) at 0°–25° C., preferably at 0°–5°

C., in the presence of an acid binding agent, suitably in the presence of pyridine or triethylamine though an excess of the starting material of the formula (III) may also be used for binding the acid.

Amine-terminal esters of the general formula (I), wherein A stands for an $-NR^5R^6$ group, n is 1 and $R^5$ as well as $R^6$ are as defined above, can be synthesized also by condensing a propionic acid of the formula (II), wherein D stands for a hydroxyl group, with an N,N-disubstituted aminoalkyl halide of the formula (IV), wherein B, $R^3$ and $R^4$ are as defined above, preferably in a solvent medium in the presence of basic substances. As solvents, alcohols, ketones or dipolar aprotic solvents, preferably isopropanol and dimethylformamide can be used; anhydrous potassium carbonate is conveniently used as basic material.

For the preparation of optically active compounds of the formula (I), particularly when the preparation of the pure enantiomers is aimed, the optically practically pure 2-[4-(5-trifluoromethyl-2-pyridyloxy)phenoxy]-propionic acid (containing more than 95% of one enantiomer) can be obtained by resolution. For the resolution process optically active basic compounds, e.g. brucine, cinchonine, chinchonidine or ephedrine, preferably (R)-(+)- or (S)-(−)-1-phenylethylamine are useful. Alcohols, ketones, acetonitrile or toluene, advantageously ethanol may be used as solvents for the fractional crystallization of the diastereomeric salt pairs. Depending on the conditions of the reaction, the condensation reactions discussed above require 2-20 hours to achieve a nearly complete conversion.

The reaction rates can be influenced by varying the temperatures though disadvantageous alterations (partial or complete racemization) should also be taken into account, particularly when optically active reactants are used at higher temperatures.

The compounds of the formula (I) possess a herbicidal effect; therefore they can be used for inhibiting the growth or injuring or completely killing the undesired plant species.

The compounds of formula (I) selectively kill the monocotyledonous weeds and thus, they can be used with advantage to damage and destroy monocotyledonous cultivated plants.

Some representatives of the compounds of formula (I) are active both when applied pre-emergence and post-emergence; thus, they can successfully be utilized against monocotyledonous weeds in dicotyledonous cultures either in the pre-emergent or post-emergent phase.

The invention further relates to herbicide compositions containing as active ingredient 0.01-95% of a compound of the formula (I) (wherein A and n are as defined above) or an optically active enantiomer thereof or a mixture of optional ratio of the enantiomers together with 5-99.99% of solid or liquid diluent, carrier, conditioning, wetting, dispersing and/or emulsifying and/or other surface active agents. Kaolin, bentonite, silica gel, talc, calcium carbonate, dolomite, Fuller's earth and gypsum etc. may be considered as solid diluents; various organic solvents such as aromatic hydrocarbons or ketones, preferably e.g. toluene, xylenes, trialkylbenzene mixtures, N-methyl-2-pyrrolidone, methylcyclohexanone or isophorone can be used as liquid diluents. Optionally, water can also preferably be used for this purpose.

The above compositions may contain both cationic, anionic or nonionic surface active agents or optionally several kinds of surface active agents.

Useful cationic surface active substances are e.g. quaternary ammonium compounds. Suitable anionic surface active agents are e.g. sulfuric acid monoester salts, e. sodium lauryl sulfate, as well as the salts of sulfonated aromatic compounds, such as calcium dodecylbenzenesulfonate and various ligninsulfonates.

The condensation product of ethylene oxide with fatty alcohols or alkylphenols, e.g. with nonylphenol as well as partial esters of long-chain fatty acids with hexitols or the condensation products thereof formed with ethylene oxide may be taken into account as suitable nonionic surface active agents.

Mineral oil fractions, soybean oil or other vegetable oil concentrates or polyethoxylated amines may be employed as activity-increasing additives which, when admixed the composition, are capable of significantly promoting the penetration to and transport in the plant of the active ingredient although they are themselves herbicidally inactive.

The compositions are prepared from the active ingredients and various additives listed above by using methods commonly employed in the industry of plant-protective agents. These compositions can be formulated in the form of powders, emulsions, suspensions, granulates and microcapsules ensuring a controlled rate of release of the active ingredient and may be used as such or usually after dilution with water.

The compositions according to the invention may optionally contain more active ingredients of the formula (I).

If necessary, other biologically active substances being different from the compounds of formula (I) may also be added to the compositions according to the invention. Since the compounds of formula (I) according to the invention are selectively active only against monocotyledonous weeds, an efficient protection of the cultivated plants can in certain cases be ensured only by using the compounds of formula of (I) in combination with other active ingredients. Such active ingredients are compounds preferably supplementing the activity of the compounds of the formula (I), i.e. substances preferably active against dicotyledonous weeds as well as contact herbicidally active agents. The agents listed hereinafter are mentioned as examples:

a) 3-isopropyl-benzo-2,1,3-thiadiazin-4-on-2,2-dioxide (bentazone);

b) phenoxyalkanecarboxylic acid, such as e.g. 4-chloro-2-methylphenoxyacetic acid (MCPA) or 2,4-dichlorophenoxyacetic acid (2,4-D);

c) dinitro-anilines, such as 2,6-dinitro-N,N-dipropyl-4-triflouromethyl-aniline (trifluralin).

d) alkylarylureas, e.g. 3-(4-bromo-3-chlorophenyl)-1-methoxy-1-methylurea (chlorbromurone);

e) thiocarbamates, e.g. N,N-di-n-propyl-S-ethyl thiocarbamate (EPIC);

f) 1,2,4-triazones, e.g. 4-amino-6-tert-butyl-4,5-dihydro-3-methylthio-1,2,4-triazin-5-one (metribuzine);

g) benzoic acids, e.g. 3,6-dichloro-2-methoxybenzoic acid (dicamba);

h) chloroacetanilides, e.g. 2-ethyl-6-methyl-N-(1-methyl-2-methoxyethyl)-chloroacetanilide (metolachlor);

i) bipyridylium salts, e.g. 1,1'-dimethyl-4,4'-bipyridylium dichloride (paraquat); and j) amino acid herbicides, e.g. N-phosponomethylglycine (glyphosate).

SPECIFIC EXAMPLES

The invention is illustrated in detail by the following non-limiting Examples. The physical characteristics, yields, reaction times and purities (determined by gas chromatography) are summarized in Table 1. The conditions for thin layer chromatography used for the examination of purity of the compounds are also indicated in Table 1. The structure of the compounds were confirmed by IR, NMR and MS spectra. The NMR spectra are given in the following form: e.g. 1.60 (d, 3H, J=7 Hz, $CH_3$-$CH_2$-) is meant as:

1.60 means the chemical shift in ppm;
d is the multiplicity of the signal;
3H is the number of protons belonging to the signal;
J is the coupling constant;
$CH_3$-$CH_2$- is the proton (group) giving the signal.

Multiplets are indicated as follows:
s: singlet
d: doublet
dd: double doublet
t: triplet
q: quartet
m: multiplet of higher order
br: broad, extending signal.

TABLE 1/A (Ia)

Structure: F₃C-pyridine-O-C₆H₄-O-CH(CH₃)-C(O)-NH-R²

| Compound No. | -R² Mol. wt. | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|
| 1 | —CH(CH₃)₂ | 1 | 33 | 85 | 100 | mp.: 130–132° C. $\alpha_D^{20} = +25.72°$ (c = 0.972%, CHCl₃) | 50.5$^a$ 46.3$^b$ 25.9$^c$ 37.0$^d$ | C: 58.69 H: 5.20 F: 15.47 N: 7.61 | 3280, 3060 2985, 1650 1505, 1335 1120, 843 | 1.125 (d, 3H, J=7Hz, 1.20 (d, 3H, J=7Hz, CH₃CH), 1.575 (d, 3H, J=7Hz, CH₃CHC(O)), 4.12 (m, 1H, (CH₃)₂CH), 4.625 (q, 1H, J=7Hz, CH₃CHC(O)), 6.275 (br, 1H, NH), 6.89–7.15 (m, 5H, arom-H+pyridine-H), 7.89 (dd, 1H, J₁=9Hz, J₂=2.5 Hz, pyridine-H), 8.42 (m, 1H, pyridine-H). | 3.68 (M⁺, 69), 349 (10), 282 (100), 268 (42), 254 (39), 238 (40), 227 (17), 146 (27), 114 (88), 86 (52). |
| 2 | —(CH₂)₃—CH₃ | 1 | 6 | 82 | 100 | mp.: 96–97° C. $\alpha_D^{20} = +12.63°$ (c = 1.029%, CHCl₃) | 55.8$^a$ 51.5$^b$ 28.0$^c$ 38.0$^d$ | C: 59.38 H: 5.54 F: 14.91 N: 7.33 | 3280, 3080 1660, 1507 1334, 1120, 1075, 840 | 0.925 (t, 3H, J=7Hz, CH₃CH₂), 1.18–1.38 (m, 2H, CH₃CH₂(CH₂)₂), 1.38–1.55 (m, 2H, CH₃CH₂CH₂CH₂), 1.60 (d, 3H, J=7Hz, CH₃CHC(O)), 3.30 (m, 2H, NHCH₂), 4.65 (q, 1H, J=7Hz, CH₃CHC(O)), 6.46 (br, 1H, NH), 6.875–7.14 (m, 5H, arom-H+pyridine-H), 7.89 (dd, 1H, J₁=9Hz, J₂=2.5Hz, pyridine-H), 8.425 (m, 1H, pyridine-H). | 3.82 (M⁺, 51), 363 (8), 282 (100), 254 (37), 238 (28), 146 (21), 128 (79), 100 (53), 57 (52) |
| 3 | —CH₂—CH=CH₂ (R)-(±) Mw: 366.34 | 2 | 10 | 91 | 99 | mp.: 89–91° C. $\alpha_D^{20} = +14.36°$ (c = 4.944%, MeOH), $\alpha_D^{20} = +20.60°$ (c = 5.193%, CHCl₃) | 51.4$^a$ ×45.8$^b$ 22.0$^c$ 32.0$^d$ | C: 59.01 H: 4.68 F: 15.56 N: 7.65 | 3285, 3090, 290, 1667, 1513, 1338, 1241, 1126, 1081, 1013, 843 | 1.61 (d, 3H, J=7Hz, CH₃CHC(O)), 3.96 (m, 2H, CH₂NH), 4.70 (q, 1H, J=7Hz, CH₃CHC(O)), 5.14 (m, 2H, CH₂:CHCH₂), 5.72–5.95 (m, 1H, CH₂:CH), 6.58 (br, 1H, NH), 6.92–7.14 (m, 5H, arom-H+pyridine-H), 7.91 (dd, 1H, J₁=9Hz, J₂=2.5Hz, pyridine-H), 8.425 (m, 1H, pyridine-H). | 366 (M⁺, 57) 347 (8), 282 (100), 254 (51), 238 (33), 227 (21), 195 (42), 146 (34), 112 (51), 83 (64), 41 (88). |
| 4 | —CH₂—CH=CH₂ (RS)-(±) M: 366.34 | 2 | 10 | 85.6 | 99.3 | mp.: 97–99° C. | 32.0$^d$ | C: 59.01 H: 4.68 F: 15.56 N: 7.65 | 3285, 3100, 3000, 1667, 1510, 1498, 1338, 1242, 1121, 1082, 1015, 840, | 1.62 (d, 3H, J=7Hz, CH₃CHC(O)), 3.94 (m, 2H, CH₂NH), 4.695 (q, qH, J=7Hz, CH₃CHC(O)), 5.13 (m, 2H, CH₂:CHCH₂), 5.72–5.94 (m, 1H, CH₂:CH), 6.57 (br, 1H, NH), 6.93–7.145 (m, 5H, arom-H+pyridine-H), 7.90 (dd, 1H, J₁=9Hz, J₂=2.5Hz, pyridine-H), 8.43 (m, 1H, pyridine-H). | |
| 5 | —CH₂—CH=CH₂ (S)-(−) Mw: 366.34 | 2 | 10 | 90 | 99.2 | mp.: 90–92° C. $\alpha_D^{20} = -13.62°$ (c = 4.991% | 32.0$^d$ | C: 59.01 H: 4.68 F: 15.56 | 3290, 3090, 2990, 1667, 1626, 1515, | 1.62 (d, 3H, J=7Hz, CH₃CHC(O)), 3.95 (m, 2H, CH₂NH), 4.70 (q, 1H, J=7Hz, CH₃CHC(O)), 5.13 (m, | |

TABLE 1/A-continued (Ia) structure: F₃C-pyridine-O-phenyl-O-CH(CH₃)-C(=O)-NH-R²

| Compound No. | -R² Mol. wt. | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|
| | | | | | | MeOH), α_D²⁰ = −19.15° (c = 4.854%, CHCl₃) | | N: 7.56 | 1497, 1341, 1244, 1127, 1083, 1016, 846 | 2H, CH₂:CHCH₂), 5.72-5.94 (m, 1H, CH₂:CH), 6.58 (br, 1H, NH), 6.92-7.15 (m, 5H, arom-H + pyridine-H), 7.90 (dd, 1H, J₁=9Hz, J₂=2.5Hz, pyridine-H), 8.43 (m, 1H, pyridine-H). | |
| 6 | 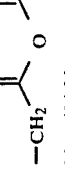 —CH₂ Mw: 406.36 | 1 | 48 | 70 | | mp.: 71-74° C. α_D²⁰ = +28.0° (c = 2.0%, CHCl₃) | 65.7ᵃ 49.0ᵇ 26.0ᶜ 33.0ᵈ | C: 59.11 H: 4.22 F: 14.03 N: 6.90 | 3265, 3060, 1656, 1506, 1334, 1198, 1120, 1078, 1012, 838 | 1.61 (d, 3H, J=7Hz, CH₃CHC(O)), 4.49 (m, 2H, CH₂NH), 4.70 (q, 1H, J=7Hz, CH₃CHC(O)), 6.19 (m, 1H, furane-H), 6.30 (m, 1H, furane-H), 6.80 (br, 1H, NH), 6.87-7.17 (m, 5H, arom-H + pyridine-H), 7.35 (m, 1H, furane-H), 7.90 (dd, 1H, J₁=9Hz, J₂=2.5Hz, pyridine-H), 8.43 (m, 1H, pyridine-H). | 406 (M⁺, 18), 387 (3), 282 (24), 254 (14), 238 (17), 152 (100), 146 (15), 81 (89) |
| 7 |  Mw: 408.41 | 1 | 16 | 92 | 99.6 | mp.: 139-141° C. α_D²⁰ = +18.8° (c = 2.0%, CHCl₃) | 62.6ᵃ 56.0ᵇ 33.9ᶜ 44.0ᵈ | C: 61.75 H: 5.68 F: 13.96 N: 6.86 | 3265, 3080, 2930, 2850, 1657, 1615, 1508, 1490, 1327, 1120, 1078, 1008, 848, 832 | 0.96-2.01 (m, 10H, cyclohexyl-H), 1.59 (d, 3H, J=7Hz, CH₃CHC(O)), 3.82 (m, 1H, cyclohexyl-H), 4.625 (q, 1H, J=7Hz, CH₃CHC(O)), 6.30 (br, 1H, NH), 6.91-7.14 (m, 5H, arom-H + pyridine-H), 7.90 (dd, 1H, J₁=9Hz, J₂=2.5Hz, pyridine-H), 8.425 (m, 1H, pyridine-H). | 408 (M⁺, 58), 389 (10), 282 (100), 268 (64), 254 (4), 238 (35), 154 (72), 126 (69), 83 (61). |
| 8 |  —CH₂ Mw: 416.39 | 1 | 16 | 90 | 99.7 | mp.: 95,97° C. α_D²⁰ = +29.2° (c = 2.0%, CHCl₃) | 60.6ᵃ 54.0ᵇ 29.6ᶜ 38.0ᵈ | C: 63.45 H: 4.60 F: 13.69 N: 6.73 | 3260, 3060, 1655, 1507, 1331, 1130, 1078, 1011, 840 | 1.64 (d, 3H, J=7Hz, CH₃CHC(O)), 4.50 (m, 2H, O-CH₂), 4.725 (q, 1H, J=7Hz, CH₃CHC(O)), 6.78 (br, 1H, NH), 6.89-7.14 (m, 5H, arom-H + pyridine-H), 7.14-7.40 (m, 5H, benzyl-arom-H), 7.88 (dd, 1H, J₁=9Hz, J₂=2.5Hz, pyridine-H), 8.425 (m, 1H, pyridine-H). | 416 (M⁺, 27), 397 (3), 282 (49), 254 (21), 238 (21), 162 (42), 134 (14), 91 (100) |

ᵃChloroform/acetone 95:5;
ᵇbenzene/acetone 8:1;
ᶜcyclohexane/ethyl acetate 3:1;
ᵈn-hexane/acetone 3:1.

TABLE 1/B (Ib) Structure: F₃C-pyridine-O-phenyl-O-CH(CH₃)-C(O)-N(R¹)R²

| Compound No. | -N(R¹)R² Mol. wt. | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|
| 9. | -N(C₂H₅)₂<br>Mw: 382.38 | 4 | 2 | 95 | 100 | mp.: 42-43.5° C.<br>$\alpha_D^{20} = +18.3°$<br>(c = 2.199%, CHCl₃) | 37.0$^a$ | C: 59.68 H: 5.54 F: 14.91 N: 7.13 | 2990, 2945, 1660, 1619, 1584, 1510, 1490, 1398, 1334, 1080, 1013, 938, 890, 838 | 1.15 (m, 6H, N(CH₂CH₃)₂), 1.61 (d, 3H, J=7Hz, CH₃CHC(O)), 3.26-3.62 (m, 4H, N(CH₂CH₃)₂), 4.93 (q, 1H, J=7Hz, CH₃CHC(O)), 6.87-7.14 (m, 5H, arom-H+pyridine-H), 7.87 (dd, 1H, J₁=9Hz, J₂=2.5Hz, pyridine-H), 8.43 (m, 1H, pyridine-H). | 382 (m⁺, 16), 363 (3), 282 (25), 254 (7), 238 (9), 146 (10), 128 (56), 100 (39), 72 (100) |
| 10. | -N(CH₂-CH=CH₂)₂<br>Mw: 406.40 | 4 | 2 | 95 | 99.2 | oil,<br>$n_D^{24} = 1.5256$,<br>$\alpha_D^{20} = +24.56°$<br>(c = 1.262%, CHCl₃) | 44.0$^b$ | C: 62.06 H: 5.21 F: 14.03 N: 6.89 | 3082, 2985, 2936, 1663, 1616, 1528, 1485, 1331, 1080, 1011, 930, 891, 837 | 1.63 (d, 3H, J=7Hz, CH₃CHC(O)), 4.05 (m, 4H, CH₂NCH₂), 4.98 (q, 1H, J=7Hz, CH₃CHC(O)), 5.02-5.27 (m, 4H, N(CH₂CH:CH₂)₂), 5.59-5.84 (m, 2H, N(CH₂CH:CH₂)₂), 6.90-7.12 (m, 5H, arom-H+pyridine-H), 7.88 (dd, 1H, J₁=9Hz, J₂=2.5Hz, pyridine-H), 8.43 (m, 1H, pyridine-H). | 406 (M⁺, 7), 387 (3), 282 (29), 254 (10), 238 (15), 152 (34), 146 (15), 124 (17), 69 (95), 47 (100) |
| 11. | pyrrolidinyl<br>Mw: 380.36 | 4 | 2 | 84 | 99.8 | mp.: 59-62° C.<br>$\alpha_D^{20} = +12.0°$<br>(c = 1.001%, CHCl₃) | 22.0$^b$ | C: 59.99 H: 5.03 F: 14.99 N: 7.37 | 2978, 2878, 1655, 1616, 1505, 1485, 1327, 1238, 1126, 1076, 1011, 887, 837 | 1.62 (d, 3H, J=7Hz, CH₃CHC(O)), 1.74-2.04 (m, 4H, NCH₂(CH₂)₂CH₂), 3.34-3.77 (m, 4H, NCH₂(CH₂)₂CH₂), 4.84 (q, 1H, J=7Hz, CH₃CHC(O)), 6.08-7.13 (m, 5H, arom-H+pyridine-H), 7.88 (dd, 1H, J₁=9 Hz, J₂=2.5 Hz, pyridine-H), 8.44 (m, 1H, pyridine-H). | 380 (M⁺, 13), 361 (4), 282 (27), 238 (16), 146 (15), 126 (100), 98 (83), 70 (31) |
| 12. | piperidinyl<br>Mw: 394.39 | 4 | 2 | 78 | 96.8 | mp.: 61-63° C.<br>$\alpha_D^{20} = +18.53°$<br>(c = 1.079%, CHCl₃) | 39.0$^b$ | C: 60.90 H: 5.37 F: 14.45 N: 7.10 | 2988, 2941, 1860, 1662, 1618, 1508, 1488, 1448, 1396, 1130, 1077, 1010, 944, 887, 834 | 1.35-1.70 (m, 6H, NCH₂(CH₂)₃CH₂), 1.625 (d, 3H, J=7Hz, CH₃CHC(O)), 3.41-3.68 (m, 4H, CH₃NCH₂), 4.96 (q, 1H, J=7 Hz, CH₃CHC(O)), 6.87-7.13 (m, 5H, arom-H+pyridine-H), 7.87 (dd, 1H, J₁=9 Hz, J₂=2.5 Hz, pyridine-H), 8.43 (m, 1H, pyridine-H) | 394 (M⁺, 10), 375 (4), 282 (22), 238 (16), 140 (63), 112 (75), 84 (100) |

$^a$ n-hexane:acetone = 4:1;
$^b$ n-hexane:acetone = 3:1;

TABLE 1/B-continued (Ib) structure: F₃C-pyridine-O-phenyl-O-CH(CH₃)-C(O)-N(R¹)R²

| Compound No. | —N(R¹)R² Mol. wt. | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|
| 13. | piperidinyl (—N< ring, 6-membered) Mw: 396.36 | 4 | 2 | 77 | 99.7 | mp: 51–53° C. $\alpha_D^{20} = +12.58°$ (c = 1.033%, CHCl₃) | 37.0[a] | C: 61.75 H: 5.68 F: 13.96 N: 6.86 | 2906, 2932, 2859, 2361, 2338, 1655, 1616, 1505, 1485, 1331, 1238, 1196, 1130, 1076, 1010, 845. | 1.42–1.85 (m, 8H, NCH₂(CH₂)₄CH₂), 1.63 (d, 3H, J=7 Hz, CH₃CHC(O)), 3.40–3.67 (m, 4H, CH₂NCH₂), 4.97 (q, 1H, J=7 Hz, CH₃CHC(O)), 6.86–7.14 (m, 5H, arom-H+pyridine-H), 7.88 (dd, 1H, J₁=9 Hz, J₂=2.5 Hz, pyridine-H), 8.43 (m, 1H, pyridine-H). | 408 (M⁺, 10), 389 (4), 282 (22), 238 (15), 154 (67), 146 (17), 126 (44), 98 (100). |
| 14. | morpholinyl (—N< with O) Mw: 396.36 | 4 | 2 | 83 | 99.9 | oil n_D²⁰ = 1.5282 $\alpha_D^{20} = +4.0°$ (c = 1.426%, CHCl₃) | 28.0[b] | C: 57.57 H: 4.83 F: 14.38 N: 7.07 | 2988, 2920, 2860, 1668, 1617, 1508, 1488, 1394, 1328, 1197, 1078, 1010, 952, 886, 838. | 1.64 (d, 3H, J=7Hz, CH₃ CHC(O)), 3.40–3.56 (m, 4H, CH₂NCH₂), 3.56–3.79 (m, 4H, CH₂OCH₂), 4.96 (q, 1H, J=7Hz, CH₃CHC(O)), 6.87–7.13 (m, 5H, arom-H+pyridine-H), 7.89 (dd, 1H, J₁=9Hz, J₂=2.5Hz, pyridine-H), 8.42 (m, 1H, pyridine-H). | 396 (M⁺, 15), 377 (5), 282 (38), 238 (18), 146 (23), 142 (52), 114 (100), 86 (26) |
| 15. | piperazinyl —N\_N—(CH₂)₂—OH Mw: 439.42 | 6 | 2 | 75[c] | 99.7 | resinous $\alpha_D^{20} = +16.39°$ (c = 0.854%, CHCl₃) | 10.0[b] | C: 57.40 H: 5.50 F: 12.97 N: 9.56 | 2930, 2815, 1655, 1620, 1511, 1492, 1400, 1334, 1130, 1082, 1015, 944, 893, 840. | 1.63 (d, 3H, J=7Hz, CH₃CHC(O)), 2.29–2.76 (m, 7H, OH + CH₂N(CH₂)CH₂), 3.55–3.85 (m, 6H, C(O)N(CH₂)CH₂ + CH₂O), 4.96 (q, 1H, CH₃CH(O)), 6.89–7.14 (m, 5H, arom-H+pyridine-H), 8.90 (dd, 1H, J₁=9Hz, J₂=2.5Hz, pyridine-H), 8.42 (m, 1H, pyridine-H). | 440 [(M+1)⁺, 4], 439 (M⁺, <1), 408 (100), 282 (17), 254 (9), 238 (11), 146 (22), 84 (38), 56 (69), 42 (47). |

[a] n-hexane/acetone = 3:1;
[b] n-hexane/acetone = 1:1;
[c] formed together with compound No. 30.

TABLE 1/C structure (Ic):
F₃C—[phenyl]—N=[pyridine]—O—[phenyl]—O—CH(CH₃)—C(O)—[O—CH₂—CH₂]ₙ—A

| Compound No. | Mol. wt. | n | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|---|
| | —N(R)R² | | | | | | | | | | | |
| 16. | —N(CH₃)₂ Mw: 398.38 | 1 | 8 | 6 | 79 | 94 | oil, n_D²⁴ = 1.5028, α_D²⁰ = +34.35° (c = 2.154%, CHCl₃) | 23.0ᵃ⁾ | C: 57.28 H: 5.31 F: 14.31 N: 7.03 | 2985, 1950, 2830, 2780, 1760, 1619, 1510, 1490, 1398, 1330, 1131, 1080, 1012, 938, 890, 836. | 1.645 (d, 3H, J=7Hz, CH₃CHC(O)), 2.27 (s, 6H, (CH₃)₂N), 2.59 (t, 2H, J=6Hz, NCH₂CH₂O), 4.30 (t, 2H, J=6Hz, OCH₂CH₂N), 4.78 (q, 1H, J=7Hz, CH₃CHC(O)), 6.89–7.19 (m, 5H, arom-H+pyridine-H), 7.875 (dd, 1H, J₁=9Hz, J₂=2.5Hz, pyridine-H), 8.43 (m, 1H, pyridine-H). | 399 [(M+1)⁺, 18], 398 (M⁺, 1), 379 (6), 282 (11), 238 (24), 146 (26), 71 (99), 58 (100), 42 (55). |
| 17. | —N(C₂H₅)₂ Mw: 426.43 | 1 | 6 | 2 | 76 | 100 | oil, n_D²⁴ = 1.5012, α_D²⁰ = +32.15° (c = 1.866%, CHCl₃) | 31.0ᵇ⁾ | C: 59.14 H: 5.91 F: 13.37 N: 6.57 | 2975, 2945, 2815, 1760, 1620, 1510, 1490, 1398, 1332, 1130, 1080, 1015, 980, 890, 838. | 1.02 (t, 6H, J=7Hz, (CH₃CH₂)₂N), 1.65 (d, 3H, J=7Hz, CH₃CHC(O)), 2.57 (q, 4H, J=7Hz, (CH₃CH₂)₂N), 2.72 (t, 2H, J=6Hz, NCH₂CH₂O), 4.26 (t, 2H, J=6Hz, OCH₂CH₂N), 4.76 (q, 1H, J=7Hz, CH₃CHC(O)), 6.89–7.11 (m, 5H, arom-H+pyridine-H), 7.88 (dd, 1H, J₁=9Hz, J₂=2.5Hz, pyridine-H), 8.435 (m, 1H, pyridine-H). | 426 (M⁺, <1), 407 (3), 282 (8), 254 (9), 238 (10), 146 (22), 86 (100) |
| | —A | | | | | | | | | | | |
| 18. | —N(C₂H₅)₂ Mw: 470.48 | 2 | 6 | 2 | 74 | —ᵈ⁾ | oil, n_D²⁰ = 1.5000, α_D²⁰ = +26.78° (c = 1.008%, CHCl₃) | 25.0ᶜ⁾ | C: 58.71 H: 6.21 F: 12.12 N: 5.96 | 2985, 2890, 2820, 1770, 1620, 1512, 1494, 1400, 1335, 1137, 1083, 1017, 946, 893, 840. | 1.03 (t, 6H, J=7Hz, (CH₃CH₂)₂N), 1.64 (d, 3H, J=7Hz, CH₃CHC(O)), 2.58 (q, 4H, J=7Hz, (CH₃CH₂)₂N), 2.66 (t, 2H, J=7Hz, NCH₂CH₂O), 3.56 (m, 2H, J=7Hz, C(O)OCH₂CH₂), 4.34 (m, 2H, C(O)OCH₂CH₂), 4.78 (q, 1H, J=7Hz, CH₃CHC(O)), 6.89–7.11 (m, 5H, arom-H+pyridine-H), 7.88 (dd, 1H, J₁=9Hz, J₂=2.5Hz, pyridine-H), 8.43 (m, 1H, pyridine-H). | 471 [(M+1)⁺, 10], 470 (M, <1), 451 (4), 282 (12), 254 (13), 238 (22), 146 (22), 86 (100), 58 (59). |

ᵃ⁾ n-hexane/acetone = 2:1;
ᵇ⁾ n-hexane/acetone = 3:1.

TABLE 1/C-continued

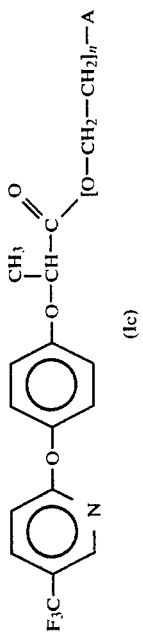

(1c)

| Compound No. | Mol. wt. | n | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|---|
| 20. | Mw: 424.31 | 1 | 8 | 6 | 85 | 97.5 | oil, $n_D^{22}$ = 1.5122, $\alpha_D^{20}$ = +33.70° (c = 1.009%, CHCl₃) | 46.0ᵃ⁾ | C: 59.43 H: 5.46 F: 13.43 N: 6.60 | 2975, 2885, 2795, 1760, 1620, 1583, 1510, 1490, 1400, 1080, 1014, 942, 890, 838. | 1.64 (d, 3H, J=7 Hz, CH₃CHC(O), 1.77 (m, 4H, NCH₂CH₂CH₂CH₂), 2.54 (m, 4H, NCH₂CH₂CH₂CH₂), 2.74 (t, 2H, J=6 Hz, NCH₂CH₂O), 4.31 (t, 2H, J=6 Hz, OCH₂CH₂N), 4.76 (q, 1H, J=7 Hz, CH₃CHC(O)), 6.88-7.12 (m, 5H, arom-H+pyridine-H), 7.87 (dd, 1H, J₁=9 Hz, J₂=2.5 Hz, pyridine-H), 3.42 (m, 1H, pyridine-H). | 424 (M⁺, <1) 405 (2), 282 (4), 254 (4), 238 (6), 169 (4), 146 (11), 84 (100), 42 (32) |
| 21. | Mw: 438.44 | 1 | 8 | 6 | 86 | 98.4 | oil, $n_D^{22}$ = 1.5115 $\alpha_D^{20}$ = +30.20° (c = 3.112%, CHCl₃) | 43.0ᵃ⁾ | C: 60.26 H: 5.75 F: 13.00 N: 6.39 | 2945, 2860, 2795, 1760, 1620, 1584, 1510, 1492, 1398, 1334, 1132, 1080, 1015, 940, 892, 838 | 1.35-1.69 (m, 6H, NCH₂(CH₂)₃CH₂), 1.64 (d, 3H, J=7 Hz, CH₃CHC(O)), 2.42 (m, 4H, NCH₂(CH₂)₃CH₂), 2.59 (t, 2H, J=6 Hz, NCH₂CH₂O), 4.31 (t, 2H, J=6 Hz, OCH₂CH₂N), 4.75 (q, 1H, J=7 Hz, CH₃CHC(O)), 6.88-7.12 (m, 5H, arom-H+pyridine-H), 7.86 (dd, 1H, J₁=9 Hz, J₂=2.5 Hz, pyridine-H), 8.43 (m, 1H, pyridine-H). | 438 (M⁺, 1), 419 (1), 383 (7), 341 (4), 282 (17), 154 (11), 146 (8), 98 (100). |
| 22. | Mw: 452.47 | 1 | 6 | 2 | 78 | 99.5 | oil, $n_D^{22}$ = 1.5178, $\alpha_D^{20}$ = +34.13° (c = 2.783%, CHCl₃) | 27.0ᵇ⁾ | C: 61.05 H: 6.02 F: 12.60 N: 6.19 | 2928, 2855, 1755, 1613, 1578, 1508, 1485, 1392, 1327, 1134, 1080, 1011, 887, 837 | 1.48-1.71 (m, 8H, NCH₂(CH₂)₄CH₂), 1.64 (d, 3H, J=7 Hz, CH₃CHC(O)), 2.63-2.75 (m, 4H, NCH₂(CH₂)₄CH₂), 2.80 (t, 2H, J=6 Hz, NCH₂CH₂O), 4.28 (t, 2H, J=6 Hz, OCH₂CH₂N), 4.75 (q, 1H, J=7 Hz, CH₃CHC(O)), 6.88-7.12 (m, 5H, arom-H+pyridine-H), 7.88 (dd, 1H, J₁=9 Hz, J₂=2.5 Hz, pyridine-H), 8.41 (m, 1H, pyridine-H). | 452 (M⁺, <1) 433 (1), 327 (8), 282 (7), 254 (16), 146 (21), 112 (100) |

ᵃ⁾n-hexane/acetone = 1:0; ᵇ⁾pure;
ᶜ⁾n-hexane/acetone = 1:2.

TABLE 1/C-continued

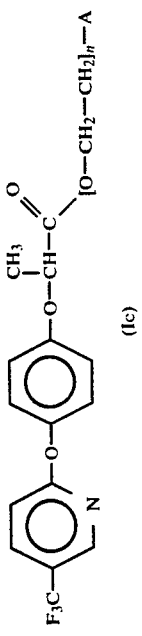
(Ic)

| Compound No. | Mol. wt. | n | Example No. | Reaction time hour | Yield % | Purity by GC | Physical data | TLC 100 × Rf | Analysis (%) Calcd. Found | IR ν(cm⁻¹) | ¹H-NMR δ(ppm) | MS m/e (%) |
|---|---|---|---|---|---|---|---|---|---|---|---|---|
| [b]n-hexane/acetone = 2:1; [c]n-hexane/acetone = 3:1. | | | | | | | | | | | | |
| 23. Mw: 440.41 (R)–(+) | | 1 | 6 | 2 | 75 | 100 | oil, $n_D^{22}$ = 1.5152, $\alpha_D^{20}$ = +37.83° (c = 2.590%, CHCl₃) | 25.0[b] | C: 57.27 H: 5.26 F: 12.94 N: 6.36 | 2965, 1865, 2820, 1758, 1618, 1582, 1508, 1488, 1393, 1011, 940, 889, 835 | 1.66 (d, 3H, J=7 Hz, CH₃CHC(O)), 2.46 (m, 4H, NCH₂CH₂OCH₂CH₂), 2.62 (t, 2H, J=6 Hz, NCH₂CH₂O), 3.67 (m, 4H, NCH₂CH₂OCH₂CH₂), 4.33 (m, 2H, OCH₂CH₂N), 4.76 (q, 1H, J=7 Hz, CH₃CHC(O)), 6.89–7.14 (m, 5H, arom-H+pyridine-H), 7.89 (dd, 1H, J₁=9 Hz, J₂=2.5 Hz, pyridine-H), 8.42 (m, 1H, pyridine-H). | 440 (M⁺, 3), 421 (2), 397 (15), 282 (5), 254 (5), 238 (4), 146 (7), 100 (100), 56 (22), 42 (21) |
| 24. (RS)–(+) Mw: 440.41 | | 1 | 6 | 2 | 81 | 100 | oil, $n_D^{22}$ = 1.5154 | 25.0[b] | C: 57.27 H: 5.26 F: 12.94 N: 6.36 | 2965, 2865, 2820, 1760, 1619, 1584, 1509, 1490, 1398, 1330, 1080, 1013, 941, 837 | 1.66 (d, 3H, J=7 Hz, CH₃CHC(O)), 2.46 (m, 4H, NCH₂CH₂OCH₂CH₂), 2.62 (t, 2H, J=6 Hz, NCH₂CH₂O), 3.66 (m, 4H, NCH₂CH₂OCH₂CH₂), 4.33 (m, 2H, OCH₂CH₂N), 4.76 (q, 1H, J=7 Hz, CH₃CHC(O)), 6.89–7.11 (m, 5H, arom-H+pyridine-H), 7.88 (dd, 1H, J₁=9 Hz, J₂=2.5 Hz, pyridine-H), 8.43 (m, 1H, pyridine-H). | |
| [c]n-hexane/acetone = 3:1; [d]n-hexane/acetone = 3:1. | | | | | | | | | | | | |
| 25. (S)–(−) M: 440.41 | | 1 | 6 | 2 | 87 | 100 | oil, $n_D^{22}$ = 1.5150, $\alpha_D^{20}$ = −36.16° (c = 2.986%, CHCl₃) | 25.0[b] | C: 57.27 H: 5.26 F: 12.94 N: 6.36 | 2965, 2865, 28280, 1760, 1617, 1582, 1509, 1490, 1398, 1330, 1080, 1013, 941, 837 | 1.66 (d, 3H, J=7Hz, CH₃CHC(O)), 2.45 (m, 4H, NCH₂CH₂OCH₂CH₂), 2.62 (t, 2H, J=6Hz, NCH₂CH₂O), 3.67 (m, 4H, NCH₂CH₂OCH₂CH₂), 4.32 (m, 2H, OCH₂CH₂N), 4.77 (q, 1H, J=7Hz, CH CHC(O), 6.88–7.14 (m, 5H, arom-H+pyridine-H), 7.89 (dd, 1H, J₁=9Hz, J₂=2.5Hz, pyridine-H), 8.44 (m, 1H, pyridine-H). | |

TABLE 1/C-continued

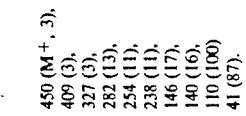

(1c)

| Compound No. | | n | Mol. wt. | Example No. | Reaction time hour | Yield % | Purity by GC | Physical data | TLC 100 × $R_f$ | Analysis (%) Calcd. Found | IR $\nu$(cm$^{-1}$) | $^1$H-NMR $\delta$(ppm) | MS m/e (%) |
|---|---|---|---|---|---|---|---|---|---|---|---|---|---|
| 26. | 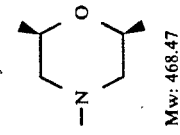 Mw: 468.47 | 1 | | 7 | 2 | 77$^f$) | 99.9 | oil, $n_D^{22}$ = 1.5075, $\alpha_D^{20}$ = +28.56° (c = 1.996%, CHCl$_3$) | 25.0$^a$) | C: 58.96 H: 5.81 F: 12.17 N: 5.98 | 1982, 1945, 2875, 1763, 1620, 1585, 1510, 1490, 1462, 1400, 1380, 1332, 1080, 1015, 890, 838 | 1.13 (d, 3H, J=6.5Hz, NCH$_2$CH(CH$_3$)O), 1.14 (d, 3H, J=6.5Hz, NCH$_2$CH(CH$_3$)O), 1.65 (d, 3H, J=7Hz, OCH(CH$_3$)C(O)), 1.70–1.87 (m, 2H, NCH$_2$CH$_2$O), 2.59 (m, 2H, NCH$_2$CHO), 2.72 (m, 2H, NCH$_2$CHO), 3.62 (m, 2H, CHOCH), 4.21–4.44 (m, 2H, OCH$_2$CH$_2$N), 4.75 (q, 1H, J=7Hz, OCH(CH$_3$)C(O)), 6.87–7.11 (m, 5H, arom-H + pyridine-H), 7.88 (dd, 1H, J$_1$=9Hz J$_2$=2.5Hz, pyridine-H), 8.425 (m, 1H, pyridine-H) | 468 (M$^+$, 4), 449 (2), 423 (4), 411 (3), 282 (10), 268 (14), 254 (6), 238 (6), 128 (100) |

$^a$)n-hexane/acetone = 3:1;
$^b$)total yield of compounds Nos. 26 and 27 (in a ratio of about 3:1);
$^c$)cyclohexane/ethyl acetate 2:1.

| 27. | 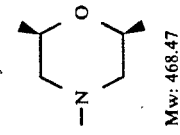 Mw: 468.47 | 1 | | 7 | 2 | 77$^g$) | 99.9 | oil, $n_D^{22}$ = 1.5085, $\alpha_D^{20}$ = 27.74° (c = 2.044%, CHCl$_3$) | 48.0$^f$) | C: 58.96 H: 5.81 F: 12.17 N: 5.98 | 2965, 2930, 2805, 1753, 1615, 1580, 1504, 1487, 1458, 1392, 1328, 1074, 1030, 1008, 883, 832 | 1.20 (d, 3H, J=6.5 Hz, NCH$_2$CH(CH$_3$)O), 1.21 (d, 3H, J=6.5 Hz, NCH$_2$CH(CH$_3$)O), 1.65 (d, 3H, J=7 Hz, OCH(CH$_3$)C(O)), 2.09–2.24 (m, 2H, NCH$_2$CH$_2$O), 2.41–2.65 (m, 4H, NCH$_2$CH(CH$_3$)OCH(CH$_3$)CH$_2$), 3.97 (m, 2H, CHOCH), 4.16–4.44 (m, 2H, OCH$_2$CH$_2$N), 4.75 (q, 1H, J=7 Hz, OCH(CH$_3$)C(O)), 6.87–7.11 (m, 5H, arom-H + pyridine-H), 7.88 (dd, 1H, J$_1$=9 Hz, J$_2$=2.5 Hz, pyridine-H), 8.43 (m, 1H, pyridine-H) | 468 (M$^+$, 9), 449 (2), 282 (12), 268 (12), 254 (10), 238 (9), 128 (100), 42 (40) |

$^a$)total yield of compounds Nos. 26 and 27 (in a ratio of about 3:1);
$^b$)cyclohexane/ethyl acetate = 2:1.

| 28. | —N(CH$_2$CH: CH$_2$)$_2$ Mw: 450.45 | 1 | | 6 | 2 | 86 | 99.7 | oil, $n_D^{22}$ = 1.5088, $\alpha_D^{20}$ = +29.88° (c = 1.164%, CHCl$_3$) | 36.0$^h$) | C: 61.32 H: 5.59 F: 12.65 N: 6.22 | 3080, 2980, 2940, 2810, 1758, 1617, 1580, 1506, 1488, 1394, 1330, 1076, 1010, 920, 886, 833. | 1.64 (d, 3H, J=7Hz, CH$_3$CHC(O)), 2.74 (t, 2H, J = 6Hz, NCH$_2$CH$_2$O), 3.13 (d, 4H, J=7Hz, N(CH$_2$CH:CH$_2$)$_2$), 4.27 (t, 2H, J=6Hz, OCH$_2$CH$_2$N), 4.75 (q, 1H, J=7Hz, CH$_3$CHC(O)), 5.06–5.29 (m, 4H, N(CH$_2$CH:CH$_2$)$_2$), 5.68–5.95 (m, 2H, N(CH$_2$CH:CH$_2$)$_2$), 6.86–7.14 (m, 5H, arom-H + pyridine-H), 7.88 (dd, 1H, | 450 (M$^+$, 3), 409 (3), 327 (3), 282 (13), 254 (11), 238 (11), 146 (17), 140 (16), 110 (100), 41 (87). |

TABLE 1/C-continued (Ic) Structure: F₃C-pyridine-O-phenyl-O-CH(CH₃)-C(=O)-[O-CH₂-CH₂]ₙ-A

| Compound No. | —A | n | Example No. | Reaction time hour | Yield % | Purity by GC | Physical data | TLC 100 × R_f | Analysis (%) Calcd. Found | IR ν(cm⁻¹) | ¹H-NMR δ(ppm) | MS m/e (%) |
|---|---|---|---|---|---|---|---|---|---|---|---|---|
| 29. | —O—N=C(CH₃)₂ Mw: 426.39 | 1 | 6 | 2 | 83 | 100 | oil, n_D²² = 1.5058 α_D²⁰ = +24.24° (c = 1.349%, CHCl₃) | 65.0ʰ⁾ 61.0ⁱ⁾ | C: 56.33 H: 4.96 F: 13.37 N: 6.57 | 3000, 2930, 2890, 1763, 1620, 1510, 1490, 1398, 1332, 1080, 1014, 940, 890, 837. | J₁=9Hz, J₂=2.5Hz, pyridine-H), 8.43 (m, 1H, pyridine-H). 1.66 (d, 3H, J=7Hz, CH₃CHC(O), 1.87 (s, 3H, N:C(CH₃)CH₃), 1.83 (s, 3H, N:C(CH₂)CH₃), 4.24 (m, 2H, CH₂ON), 4.43 (m, 2H, C(O)OCH₂), 4.78 (q, 1H, J=7Hz, CH₃CHC(O)), 6.89-7.13 (m, 5H, arom-H + pyridine-H), 7.88 (dd, 1H, J₁=9Hz, J₂=2.5Hz, pyridine-H), 8.44 (m, 1H, pyridine-H). | 426 (M⁺, 26) 407 (3), 370 (10), 354 (17), 282 (61), 254 (34), 238 (18), 146 (22) 100 (26). |
| 30. | —N(piperazine)N—Acilᵃ⁾ Mw: 748.66 | 1 | 6 | 2 | 65 | —ᵏ⁾ | resinous α_D²⁰ = +33.36° (c = 0.998%, CHCl₃) | 57.0ʰ⁾ | C: 57.75 H: 4.58 F: 15.23 N: 7.48 | 2995, 1945, 2820, 1767, 1740, 1648, 1620, 1508, 1490, 1397, 1330, 1133, 1080, 1013, 942, 890, 837. | 1.625 (m, 5H, 2 × CH₃CHC(O)), 2.23-2.53 (m, 4H, O(CH₂)₂N—(CH₂)CH₂), 2.60 (m, 2H, NCH₂CH₂O), 3.52-3.75 (m, 4H, C(O)N(CH₂CH₂), 4.30 (m, 2H, OCH₂CH₂N), 4.76 (q, 1H, J=7Hz, CH₃CHC(O)O), 4.95 (q, 1H, J=7Hz, CH₃CHC(O)N), 6.87-7.13 (m, 10H, 2 × arom-H + pyridine-H), 7.88 (dd, 2H, J₁=9Hz, J₂=2.5Hz, 2 × pyridine-H) 8.41 (m, 2H, 2 × pyridine-H). | |

ʰ⁾n-hexane/acetone = 5:1;
ⁱ⁾n-hexane/acetone = 3:1;
ʲ⁾n-hexane/ethyl acetate = 7:3.

ᵃ⁾Acyl means 2-[4-(5-trifluoromethyl-2-pyridyloxy)phenoxy]propionyl;
ᵏ⁾pure according to TLC;
ᶠ⁾n-hexane/acetone = 1:1.

TABLE 1/D

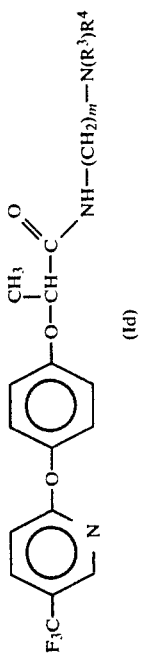

(Id)

| Compound No. | —N(R³)R⁴ Mol. wt. | m | Example No. | Reaction time hour | Yield % | Purity by GC | Physical data | TLC 100 × $R_f$ | Analysis (%) Calcd. Found | IR ν(cm⁻¹) | ¹H-NMR δ(ppm) | MS m/e (%) |
|---|---|---|---|---|---|---|---|---|---|---|---|---|
| 31. | —N(CH₃)₂ Mw: 397.39 | 2 | 10 | 10 | 73 | 99.8 | mp: 50–51° C. $\alpha_D^{20} = +15.41°$ (c = 2.919%, CHCl₃) | 55.0[a] | C: 57.42 5.58 H: F: 14.34 N: 10.57 | 3292, 2985, 2950, 2830, 2780, 1662, 1622, 1510, 1490, 1395, 1334, 1125, 1078, 1012, 930, 890, 840 | 1.60 (d, 3H, J=7Hz, CH₃CHC(O)), 2.18 (s, 6H, N(CH₃)₂), 2.23–2.42 (m, 2H, NCH₂), 3.34 (m, 2H, NHCH₂), 4.66 (q, 1H, J=7Hz, CH₃CHC(O)), 6.90–7.14 (m, 6H, NH+arom-H+pyridine-H), 7.88 (dd, 1H, J₁=9Hz, J₂=2.5Hz, pyridine-H), 8.40 (m, 1H, pyridine-H). | 398 [(M + 1)⁺, 43], 282 (5), 238 (14), 146 (9), 71 (95), 58 (100), 42 (27). |
| 32. | —N(CH₃)₂ Mw: 411.41 | 3 | 10 | 10 | 80 | 100 | mp: 36–38° C. $\alpha_D^{20} = +14.29°$ (c = 2.427%, CHCl₃) | 36.0[b] | C: 58.38 H: 5.88 F: 13.85 N: 10.21 | 2980, 2945, 2825, 1675, 1618, 1508, 1490, 1396, 1332, 1078, 1012, 937, 888, 835. | 1.59 (d, 3H, J=7Hz, CH₃CHC(O)), 1.54–1.72 (m, 2H, CH₂CH₂CH₂), 2.13 (s, 6H, N(CH₃)₂), 2.26–2.40 (m, 2H, CH₂N), 3.39 (m, 2H, NHCH₂), 4.64 (q, 1H, J=7Hz, CH₃CHC(O)), 6.88–7.15 (m, 5H, arom-H+pyridine-H), 7.88 (dd, 1H, J₁=9Hz, J₂=2.5Hz, pyridine-H), 7.88–8.00 (m, 1H, NH), 8.40 (m, 1H, pyridine-H). | 412 [(M + 1)⁺, 50], 411 (M⁺, 13), 339 (36), 282 (12), 238 (24), 129 (45), 84 (51), 72 (77), 58 (100). |
| 33. | —N(C₂H₅)₂ Mw: 425.44 | 2 | 9 | 2 | 76 | 100 | oil, $n_D^{20} = 1.5144$ $\alpha_D^{20} = +14.2°$ (c = 1.690%, CHCl₃) | 60.0[b] | C: 59.28 H: 6.16 F: 13.40 N: 9.88 | 3330, 2980, 2950, 2825, 1682, 1622, 1492, 1440, 1332, 1081, 1015, 940, 892, 849. | 0.96 (t, 6H, J=7.5Hz, N(CH₂CH₃)₂), 1.60 (d, 3H, J=7Hz, CH₃CHC(O)), 2.42–2.67 (m, 2H, NCH₂), 2.48 (q, 4H, J=7Hz, N(CH₂CH₃)₂), 3.33 (m, 2H, NHCH₂), 4.66 (q, 1H, J=7Hz, CH₃CHC(O)), 6.88–7.13 (m, 5H, arom-H+pyridine-H), 7.18 (br, 1H, NH), 7.88 (dd, 1H, J₁=9Hz, J₂=2.5Hz, pyridine-H), 8.42 (m, 1H, pyridine-H). | 425 (M + 1, 7), 383 (7), 282 (15), 254 (9), 146 (7), 86 (100). |
| 34. | —N(C₂H₅)₂ Mw: 439.46 | 3 | 9 | 2 | 84 | 97.2 | oil, $n_D^{20} = 1.5128$ $\alpha_D^{20} = +15.02°$ (c = 1.00%, CHCl₃) | 67.0[b] 19.0[c] | C: 60.12 H: 6.42 F: 12.97 N: 9.56 | 3330, 2975, 2945, 2815, 1676, 1618, 1510, 1490, 1398, 1130, 1080, 1014, 940, 890, 838. | 0.97 (t, 6H, J=7.5Hz, N(CH₂CH₃)₂), 1.58 (d, 3H, J=7Hz, CH₃CHC(O)), 1.47–1.76 (m, 2H, CH₂CH₂CH₂), 2.30–2.61 (m, 6H, CH₂N(CH₂CH₃)₂), 3.18–3.58 (m, 2H, NHCH₂), 4.62 (q, 1H, J=7Hz, CH₃CHC(O)), 6.88–7.13 (m, 5H, arom-H+pyridine-H), 7.88 (dd, 1H, J=9Hz, J=2.5Hz, pyridine-H), 7.98 (br, 1H, NH), 8.42 (m, 1H, pyridine-H). | 440 (M + 1)⁺, 6], 439 (M⁺, 2), 410 (15), 367 (11), 282 (8), 238 (9), 146 (15), 86 (100), 72 (65). |

[a]methanol/benzene = 9:1;
[b]methanol/benzene = 7:3;

TABLE 1/D-continued

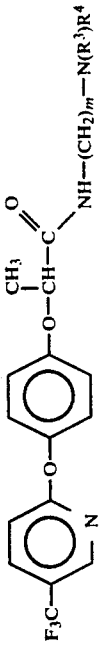
(Id)

| Compound No. | -N(R³)R⁴ Mol. wt. | m | Example No. | Reaction time hour | Yield % | Purity by GC | Physical data | TLC 100 × $R_f$ | Analysis (%) Calcd. Found | IR $\nu$(cm⁻¹) | ¹H-NMR δ(ppm) | MS m/e (%) |
|---|---|---|---|---|---|---|---|---|---|---|---|---|
| 35. | [pyrrolidinyl] Mw: 423.42 | 2 | 9 | 2 | 77 | 97.2 | mp: 71–7.25° C. $\alpha_D^{20} = +22.41°$ (c = 1.00% CHCl₃) | 46.0[b] | C: 59.56 H: 5.71 F: 13.46 N: 9.92 | 3330, 2980, 2945, 2885, 2805, 1680, 1620, 1510, 1490, 1398, 1332, 1080, 1012, 940, 890, 837 | 1.60 (d, 3H, J=7 Hz, CH₃CHC(O)), 1.71 (m, 4H, NCH₂(CH₂)₂CH₂), 2.33–2.71 (m, 6H, CH₂N(CH₂)CH₂), 3.38 (m, 2H, NHCH₂), 4.66 (q, 1H, J=7 Hz, CH₃CHC(O)), 6.8–7.13 (m, 6H, NH+arom-H+pyridine-H), 7.88 (dd, 1H, J₁=9 Hz, J₂=2.5 Hz, pyridine-H), 8.41 (m, 1H, pyridine-H). | 424 [(M + 1)⁺, 3], 423 (M⁺, 1) 282 (5), 254 (5), 146 (9), 97 (30), 84 (100), 42 (46), 58 (43). |
| 36. | [piperidinyl] Mw: 437.45 | 2 | 9 | 2 | 85 | 98.0 | mp: 60–63° C. $\alpha_D^{20} = +27.36°$ (c = 1.00%, CHCl₃) | 69.0[a] 29.0[b] | C: 60.40 H: 5.99 F: 13.03 N: 9.61 | 3340, 2940, 2855, 2810, 1680, 1620, 1505, 1488, 1396, 1331, 1079, 1012, 937, 888, 835. | 1.31–1.61 (m, 6H, NCH₂(CH₂)₃CH₂), 1.61 (d, 3H, J=7 Hz, CH₃CHC(O)), 2.18–2.54 (m, 6H, CH₂N(CH₂)CH₂), 3.35 (m, 2H, NHCH₂), 4.66 (q, 1H, J=7 Hz, CH₃CHC(O)), 6.91–7.13 (m, 5H, arom-H+pyridine-H), 7.18 (br, 1H, NH), 7.88 (dd, 1H, J₁=9 Hz, J₂=2.5 Hz, pyridine-H), 8.41 (m, 1H, pyridine-H). | 438 [(M + 1)⁺, 1], 437 (M⁺, <1) 418 (3), 282 (9), 254 (11), 238 (16), 146 (22), 98 (100) |
| 37. | [morpholinyl] Mw: 439.42 | 2 | 9 | 2 | 75 | 99.8 | mp: 70.6–72° C. $\alpha_D^{20} = +23.92°$ (c = 2.20% CHCl₃) | 46.0[c] | C: 57.40 H: 5.50 F: 12.97 N: 9.56 | 3325, 2965, 2825, 1655, 1622, 1510, 1491, 1398, 1344, 1335, 1240, 1130, 1080, 1012, 940, 870, 840. | 1.62 (d, 3H, J=7Hz, CH₃CHC(O)), 2.24–2.58 (m, CH₂N(CH₂)CH₂), 3.21–3.52 (m, 2H, NHCH₂), 3.59 (m, 4H, CH₂OCH₂), 4.65 (q, 1H, J=7Hz, CH₃CHC(O)), 6.87–7.15 (m, 6H, NH+arom-H+pyridine-H), 7.89 (dd, 1H, J₁=9Hz, J₂=2.5Hz, pyridine-H), 8.40 (m, 1H, pyridine-H). | 440 [(M + 1)⁺, 4], 439 (M⁺, 1), 420 (2), 282 (8), 238 (12), 146 (15), 100 (100), 56 (69). |

[a] methanol/benzene = 9:1;
[b] n-hexane/acetone = 3:1;
[c] n-hexane/acetone = 1:2;
[d] methanol/benzene = 7:3.

[e] n-hexane/acetone = 1:2.

EXAMPLE 1

Preparation of
N-(n-butyl)-2-[4-(5-trifloromethyl-2-pyridyloxy)-phenoxy]-propionic acid amide (compound No. 2)

A mixture containing 17.1 g (0.05 mol) of methyl 2-[4-(5-trifluoromethyl-2-pyridyloxy)-phenoxy]-propionate and 7.3 g (0.1 mol) of n-butylamine is heated at 80°–85° C. for 6 hours while stirring, then cooled and diluted with 50 ml of benzene. The benzene solution is shaken with 5% aqueous hydrochloric acid solution and then washed with water to acid-free. After separation the organic phase is dried over anhydrous sodium sulfate and evaporated to dryness. The crude product can be recrystallized from a mixture of benzene with petroleum ether (b.p. 70° C.) The compounds Nos. 1, 6, 7 and 8 are similarly prepared from the corresponding starting materials.

EXAMPLE 2

Preparation of
N-allyl-2-[4-(5-trifluoromethyl-2-pyridyloxy)phenoxy]-propionic acid amide (compound Nos. 3, 4 and 5)

A mixture containing 11.85 g (0.035 mol) of methyl 2-[4-(5-trifluoromethyl-2-pyridyloxy)phenoxy]-propionate and 11.5 g (0.2 mol) of allylamine is boiled under reflux (about 60° C.) for 10 hours. (The reaction is followed by gas chromatography.) Thereafter, the excess of allylamine is distilled off and the residue is dissolved in benzene. After washing the solution cooled down with 5% aqueous hydrochloric acid and then with saturated sodium chloride solution, the organic phase is dried over anhydrous magnesium sulfate and evaporated. The crude product is recrystallized from petroleum ether (b.p. 120° C.) containing a small amount of toluene.

EXAMPLE 3

Preparation of methyl 2-[4-(5-trifluoromethyl-2-pyridyloxy)phenoxy]-propionate a) To a solution containing 127.5 g (0.5 mol) of 4-(5-trifluoromethyl-2-pyridyloxy)-phenol in 440 ml of anhydrous toluene 20.4 g (0.51 mol) of powered sodium hydroxide are added at 80° C. and then, after 60 minutes an additional amount of 28.6 g (0.71 mol) of sodium hydroxide are added. After cooling down the mixture to 40° C., 80.6 g (0.65 mol) of methyl 2-chloropropionate are portionwise added while maintaining the temperature at 50°–55° C.

After a reaction time of 5 hours the mixture is heated to 90° C. for 30 minutes, then 500 ml of water are continuously added in portions while distilling the reaction mixture to remove methanol. The aqueous phase of the two-phase system obtained is further processed by adding 300 ml of toluene and then acidified to pH 1 at 40° C. by adding 96% sulfuric acid. After stirring the reaction mixture at 80° C. for a short period the phases are separated in hot state. When 2-[4-(5-trifluoromethyl-2-pyridyloxy)phenoxy]propionic acid is desired, the toluene solution is dried, clarified by using activated charcoal and evaporated to dryness; whereas for preparing the methyl ester, 30 g (0.94 mol) of methanol and 14.2 g (0.14 mol) of 96% sulfuric acid are weighed to the anhydrous toluene solution and the esterification is carried out at 55° C. After washing and drying, the toluene solution is evaporated to dryness to obtain a thick oily residue which solidifies after mixing with n-hexane and scratching. For preparing the (R)-(+)-enantiomer of the acid or methyl ester, respectively, methyl (S)-(−)-2-chloropropionate is used.

b) A mixture containing 12.46 g of 2-[4-(5-trifluoromethyl-2-pyridyloxy)phenoxy]propionic acid and a catalytic amount of p-toluenesulfonic acid in 70 ml of methanol is boiled under reflux for 4 hours. After evaporating the solution to dryness, the residue is dissolved in ether and washed with sodium hydrogen carbonate solution. The ethereal layer is separated, dried over anhydrous magnesium sulfate and evaporated to dryness to give 11.5 g of product.

EXAMPLE 4

Preparation of
N,N-diethyl-2-[4-(5-trifluoromethyl-2-pyridyloxy)-phenoxy]propionic acid amide (compound No. 9)

3.4 g (0.046 mol) of diethylamine and 4.8 g (0.47 mol) of triethylamine dissolved in 10 ml of benzene are dropped into the solution of 15.6 g (0.045 mol) of 2-[4-(5-trifluoromethyl-2-pyridyloxy)phenoxy]propionyl chloride in 40 ml of anhydrous benzene at 0°–5° C. under stirring. After termination of the portionwise addition, the reaction mixture is stirred for additional 2 hours whilst it is allowed to warm to room temperature. The mixture is filtered off, the precipitate is washed with a little volume of ether, the filtrate is washed first with 5% hydrochloric acid and then with saturated sodium chloride solution, then dried over anhydrous magnesium sulfate and finally evaporated to dryness. The crude product is purified by chromatography on a column filled with silica gel of 0.063–0.2 mm particle size by using a 4:1 mixture of n-hexane/acetone for elution.

The compounds Nos. 10–14 are similarly prepared from the corresponding amines as starting substances.

EXAMPLE 5

Preparation of
2-[4-(5-trifluoromethyl-2-pyridyloxy)phenoxy]propionyl chloride 13.1 g (0.04 mol) of 2-[4-(5-trifluoromethyl-2-pyridyloxy)phenoxy]propionic acid (prepared according to example 3 a)) are reacted with 31.4 g (0.25 mol, about 20 ml) of thionyl chloride by boiling under reflux while continuously introducing nitrogen and constantly stirring for 3 hours. After distilling off the excess thionyl chloride with exclusion of moisture under reduced pressure, a distillation residue is obtained which can be directly used for further transformation.

EXAMPLE 6

Preparation of 2'-(4-morpholino)ethyl 2-[4-(5-trifluoromethyl-2-pyridyloxy)phenoxy]propionate (compounds Nos. 23, 24 and 25)

A solution containing 13.9 g (0.04 mol) of 2-[4-(5-trifluoromethyl-2-pyridyloxy)phenoxy]propionyl chloride in 20 ml of toluene is cooled to 0° C. and a mixture containing 5.54 g (0.042 mol) of 4-(2-hydroxyethyl)morpholine and 4.25 g (0.042 mol) of triethylamine in 20 ml of toluene are added dropwise at a temperature range between 0° C. and 5° C. under constant stirring. After the addition the mixture is stirred at 0°–5° C. for additional 2 hours and then allowed to stand overnight.

The mixture is filtered off and the precipitate is washed with a little volume of ether. After washing the combined filtrate and washing the liquid with water and then with saturated sodium chloride solution, it is dried over anhydrous magnesium sulfate, clarified by using activated charcoal and evaporated to dryness. The crude product is purified by chromatography on a column filled with silica gel of 0.063–0.2 mm particle size by using a 4:1 mixture of n-hexane/acetone for elution. The purity of the obtained product is checked by gas chromatography.

Any of the compounds Nos. 16–30 can be prepared similarly by using the corresponding starting materials.

EXAMPLE 7

Preparation of cis and trans-2'-(2,6-dimethyl-4-morpholino)ethyl (R)-(+)-2-[4-(5-trifluoromethyl-2-pyridyloxy)phenoxy]propionate (compounds Nos. 26 and 27)

The title compounds are prepared as described in Example 6 by reacting (R)-(+)-2-[4-(5-trifluoromethyl-2-pyridyloxy)phenoxy]propionyl chloride with an about 3:1 mixture of the cis and trans isomers of 2-(2,6-dimethyl-4-morpholino)ethanol as starting materials. The product, which is an isomeric mixture, is separated to its components by chromatography on a column filled with silica gel of 0.063–0.2 mm particle size by using a 2:1 mixture of cyclohexanone/ethyl acetate for elution.

EXAMPLE 8

Preparation of 2'-(1-piperidino)ethyl-2-[4-(5-trifluoromethyl-2-pyridyloxy)phenoxy]propionate (compound No. 21)

After suspending 0.2 g of potassium iodide and 33.2 g (0.24 mol) anhydrous, powdered potassium carbonate in a solution of 32.8 g (0.1 mol) of 2-[4-(5-trifluoromethyl-2-pyridyloxy)phenoxy]propionic acid in 120 ml of dimethylformamide 18.5 g (0.1 mol) of 1-(2-chloroethyl)-piperidine hydrochloride dissolved in dimethylformamide are added while stirring. After heating at 78°–80° C. for 6 hours the reaction mixture is filtered, the filtrate is made free from solvent under reduced pressure and the residue is boiled with 150 ml of petroleum ether (b.p. 70° C.). The solution is decanted from the undissolved material, clarified by activated charcoal, filtered and evaporated to dryness to give a lemon-yellow oily residue. If desired, this product may further be purified by chromatography on a silica gel column.

The compounds Nos. 17 and 20 are similarly prepared from the corresponding starting materials.

EXAMPLE 9

Preparation of N-[2-(1-pyrrolidino)ethyl]-2-[4-(5-trifluoromethyl-2-pyridyloxy)phenoxy]propionic acid amide (compound No. 35)

A mixture of 12.8 g (0.112 mol) of 1-(2-aminoethyl)-pyrrolidine, 12.5 g (0.123 mol, about 17.2 ml) of triethylamine and 25 ml of benzene are added dropwise to the solution of 38.7 g (0.112 mol) of 2-[4-(5-trifluoromethyl-2-pyridyloxy)phenoxy]propionyl chloride in 50 ml of benzene under cooling and stirring at 5°–10° C. After the addition, the reaction mixture is stirred at room temperature for additional 2 hours and then filtered. The filtrate is clarified by activated charcoal and evaporated to dryness. The purity of the obtained product is checked by gas chromatography.

Compounds Nos. 33, 34, 36 and 37 are similarly prepared by using the corresponding, asymmetrically di-substituted alkylenediamines as starting materials.

EXAMPLE 10

Preparation of N-(2-diethylaminoethyl)-2-[4-(5-trifluoromethyl-2-pyridyloxy)phenoxy]propionic acid amide (compound No. 31)

34.2 g (0.1 mol) of methyl 2-[4-(5-trifluoromethyl-2-pyridyloxy)phenoxy]propionate are heated with 13.2 g (0.15 mol) of 2-dimethylaminoethylamine at 80° C. for 10 hours under stirring. After cooling down, the reaction mixture is washed out from the reactor by using acetone and the obtained solution is evaporated to dryness. After boiling the residue with petroleum ether (b.p. 70° C.) containing a little amount of benzene, the solution is decanted, treated with activated charcoal, filtered off and evaporated to dryness. The oily residue slowly becomes crystalline. The progress of the reaction and the purity of the product obtained are checked by gas chromatography.

Compound No. 32 is similarly prepared, except that 3-dimethylamino-1-propylamine is used as starting material instead of 2-dimethylaminoethylamine.

EXAMPLE 11

Preparation of (RS)-(+)-2-[4-(5-trifluoromethyl-2-pyridyloxy)phenoxy]propionic acid 100.0 g (0.92 mol) of (RS)-(+)-2-chloropropionic acid are added to the solution of 192.0 g (0.75 mol) of 4-(5-trifluoromethyl-2-pyridyloxy)phenol in 900 g (about 1050 ml) of xylene. The temperature of the reaction mixture is elevated to 80° C. and 78.0 g (1.95 mol) of sodium hydroxide dissolved in water are added dropwise under such a reduced pressure (about 36 kPa) that the mixture boils at 90° C. The water formed in the reaction is continuously distilled off while maintaining the boiling temperature at 90° C. After the addition, the reaction mixture is stirred at 90° C. for additional 15 minutes, then the reduced pressure is ceased. After adding 300 ml of water to the mixture and stirring at 85° C. for 10 minutes, it is acidified by adding phosphoric acid and the phases are separated. The xylene layer is dried, treated with activated charcoal and finally evaporated to dryness.

EXAMPLE 12

Resolution of (RS)-(±)-2-[4-(5-trifluoromethyl-2-pyridyloxy)phenoxy]propionic acid a) Preparation of (S)-(-9-2-[4-(5-trifluoromethyl-2-pyridyloxy)phenoxy]-propionic acid After dissolving 116.4 g (0.36 mol) of racemic acid (prepared e.g. as described in Example 11) in 120 ml of abs. ethanol by heating the possibly present insoluble impurities are removed from the solution by filtration and 43.32 g (0.36 mol) of (S)-(−)-1-phenylethylamine dissolved in 20 ml of ethanol are added. The solution is treated with activated charcoal, filtered and after cooling it is set aside in a refrigarator at −18° C. for crystallization. It is advisable to inoculate the solution when a crystal seed is available. The precipitated diastereomeric salt is enriched by several (at least three) fractional crystallizations. For setting free the acid 19.7 g of the diastereomeric salt are mixed with 30 ml of 18% aqueous hydrochloric acid, the aqueous solution is extracted with 50 ml of ether and this operation is repeated twice with 30 ml of ether each. After combination the ethereal phase is washed with saturated sodium chloride solution, dried over anhydrous magnesium sulfate and the solvent is completely removed to obtain 13.9 g of acid as a thick, viscous, pale yellow oil. $[\alpha]_D^{20} = -25.3°$ (methanol).

In order to examine the optical purity a little part of the acid (2.0–2.5 g) is converted to its methyl ester and the ratio of enantiomers is determined by separation on a chiral HPLC column. Based on this method, the purity of methyl ester obtained and consequently, that of the acid is higher than 99% ee, $[\alpha]_D^{20} = -40.0°$ (methanol).

b) Preparation of (R)-(+)-2-[4-(5-trifluoromethyl-2-pyridyloxy)phenoxy]propionic acid The process described under a) is followed, except that (R)-(+)-1-phenylethylamine is used as resolving agent.

For obtaining the diastereomeric salt, the racemic acid may also be used as starting material, however, it is preferable to use 2-[4-(5-trifluoromethyl-2-pyridyloxy)-phenoxy]propionic acid obtained from the combined diastereomeric salt fractions which are enriched in (R)-(+)-enantiomer in the course of resolution described under a).

The $[\alpha]_D^{20}$ value of the acid thus obtained is 24.93° (methanol); based on the determination on chiral HPLC, the purity of the methyl ester and consequently, that of the acid are higher than 99% ee. The $[\alpha]_D^{20}$ value of the methyl ester was found to be $-39.7°$ (methanol).

EXAMPLE 13

Preparation of herbicide compositions a) Emulsifiable concentrate 125 parts by weight of the compound No. 23 are dissolved in a solution containing 25 parts by weight (abbreviated hereinafter as: pbw) of Arylan CA (calcium dodecylbenzenesulfonate), 250 pbw of Synperonic NX (ethoxylated nonylphenol) and 525 pbw of Solvesso 100. Thus a concentrate with 125 g/liter concentration of active ingredient is obtained which is diluted to the desired active ingredient content by adding water before the use.

b) Emulsifiable concentrate 80 pbw of compound No. 3 are dissolved in a solution containing 50 pbw of Phenylsulfonate CALX (calcium dodecylbenzenesulfonate), 50 pbw of Synperonic NX (ethoxylated nonylphenol) and 800 pbw of Aromasol-H, then the volume of the solution is supplemented to 1000 ml by adding Aromasol-H. The emulsifiable concentrate thus obtained is diluted to the desired active ingredient content by adding water before the use.

c) Wettable powder 50 pbw of compound No. 1
5 pbw of silica gel
39 pbw of kaolin
5 pbw of sodium ligninsulfonate and
1 pbw of sodium lauryl sulfate are mixed and homogenized, then ground to a powder with a particle size lower than 50 microns.

d) Combined composition 20 g of N-phosphonomethylglycine, 40 g of compound No. 16, 50 ml of water, 50 ml of paraffin oil and 10 g polyethyleneoxide-diol are mixed to a uniform cream which is then converted to an emulsion being useful for spraying by adding water to achieve the desired dilution.

e) Combined composition 10 g of compound No. 17, 2 g of 4-chloro-2-methylphenoxyacetic acid, 10 g of paraffin oil and 8 g of fatty acid polyglycol ester are dissolved in 70 g of xylene. The concentrate obtained is diluted to the desired volume by adding water before the use.

EXAMPLE 14

Investigation of the pre-emergent herbicidal activity

After placing 200 g of earth each into paper boxes of 200 cm² surface perforated on their lower side, seeds of the test plants were sown on the earth. The seeds were covered by tillable soil of 1.5 cm in depth and sprayed with various doses of the chemicals. The spray solutions were prepared by using nonionic surface active additive in a known way and applied after dilution with water to the desired volume.

After spraying, the boxes were placed onto handling trays of 40×50 cm fitted with an adsorbing cloth on their lower part (each treated box was put onto a separate tray to avoid the leaking of the active ingredients of the individual treatments). The supplementation of water was ensured by maintaining the adsorbing cloth in a wet state. The effects of the test compounds were optically evaluated in comparison to the untreated controls by using en evaluating score of 0 to 3 at the end of the 2nd and 4th weeks, respectively following treatment. The score was as follow:

| | |
|---|---|
| 0: | no plant injury |
| 0.5: | plant injury of 1–15% |
| 0.5–1.5: | plant injury of 15–50% |
| 1.5–2.5: | plant injury of 50–75% |
| 2.5–3.0: | plant decay of 75–100%. |

The results are summarized in Table 2.
In the Tables the following abbreviations are used:
AV: wild-oat (*Avena fatua*)
Ec: barnyard grass (*Echinochloa crus-galli*)
Sg: bristle grass (*Setaria glauca*)
Ag: wheat-grass (*Agropyron repens*)
Al: meadow foxtail (*Alopecurus myosuroides*)
Ap: silky bent grass (*Apera spice venti*)
Sh: Guinea-grass (*Sorghum halepense*)
Pm: cultivated millet (*Panicum miliaceum*)
Dg: Italian millet (*Digitaria sanguinalis*)
Wh: wheat
Ri: rice (*Otyza sativa*)
Ma: maize
Am: ambrosia (ragweed) (*Ambrosia elatior*)
Ca: white goose-foot (*Chenopodium album*)
Sa: white mustard (*Sinapis alba*)
Ar: pilous amaranth (*Amaranthus retroflexus*)
Ga: burweed (*Galium aparine*)

Mi: scentless matricaria (*Matricaria inodora*)
Sn: black nightsade (*Solanum nigrum*)
Pl: burdock persicary (*Polygonum lapathifolium*)
Sb: sugar beet
S: soy
Sf: sunflower
To: tomato
Af: alfalfa relative moisture content varied between 70 and 85%. The activity of the compounds was evaluated on the 14th day in comparison to the untreated controls by using the evaluation score from 0 to 3 described in Example 14. The results are summarized in Table 3.

The selectivity of the activity of the compounds is also well illustrated by the data of the Table.

TABLE 2

| Compound No. | Active ingred. kg/ha | Pre-emergent herbicidal effect Herbicidal effect |||||||||||||||||||||||
|---|---|---|---|---|---|---|---|---|---|---|---|---|---|---|---|---|---|---|---|---|---|---|---|
| | | Monocotyledonous test plants |||||||||||Dicotyledonous test plants ||||||||||||
| | | Av | Ec | Sg | Ag | Al | Ap | Sh | Pm | Wh | Ri | Ma | Am | Ca | Sa | Ar | Ga | Mi | Sn | Pl | Sb | S | Sf | To | Af |
| 1 | 2.0 | 2 | 3 | 3 | 3 | 3 | 3 | 3 | 3 | 3 | 3 | 3 | 0 | 0 | 0 | 0 | 0 | 0 | 0 | 0 | 0 | 0 | 0 | 0 | 0 |
| 2 | 1.0 | 1 | 3 | 3 | 2 | 3 | 2 | 3 | 3 | 2 | 2 | 3 | 0 | 0 | 0 | 0 | 0 | 0 | 0 | 0 | 0 | 0 | 0 | 0 | 0 |
| 1 | 0.5 | 0 | 3 | 2 | 2 | 2 | 2 | 3 | 3 | 2 | 0 | 2 | 0 | 0 | 0 | 0 | 0 | 0 | 0 | 0 | 0 | 0 | 0 | 0 | 0 |
| 3 | 2.0 | 3 | 3 | 3 | 3 | 3 | 3 | 3 | 3 | 3 | 3 | 3 | 0 | 0 | 0 | 0 | 0 | 0 | 0 | 0 | 0 | 0 | 0 | 0 | 0 |
| 3 | 1.0 | 1 | 3 | 3 | 3 | 3 | 3 | 2 | 3 | 2 | 2 | 2 | 0 | 0 | 0 | 0 | 0 | 0 | 0 | 0 | 0 | 0 | 0 | 0 | 0 |
| 3 | 0.5 | 0 | 2 | 2 | 1 | 2 | 2 | 2 | 3 | 2 | 2 | 2 | 0 | 0 | 0 | 0 | 0 | 0 | 0 | 0 | 0 | 0 | 0 | 0 | 0 |
| St. | 2.0 | 2 | 3 | 3 | 3 | 3 | 3 | 3 | 3 | 3 | 3 | 3 | 0 | 0 | 0 | 0 | 0 | 0 | 0 | 0 | 0 | 0 | 0 | 0 | 0 |
| St. | 1.0 | 1 | 3 | 3 | 2 | 3 | 2 | 2 | 3 | 2 | 3 | 3 | 0 | 0 | 0 | 0 | 0 | 0 | 0 | 0 | 0 | 0 | 0 | 0 | 0 |
| St. | 0.5 | 0 | 3 | 0 | 0 | 3 | 2 | 0 | 3 | 0 | 1 | 1 | 0 | 0 | 0 | 0 | 0 | 0 | 0 | 0 | 0 | 0 | 0 | 0 | 0 |

St: means the standardized control, i.e. fluazifop-P-butyl, chemically (R)-(+)-n-butyl-2-/4-(5-trifluoromethyl-2-pyridyloxy)-phenoxy/propionate

EXAMPLE 15

Investigation on the post-emergent herbicidal effect

Plastic dishes of 200 ml volume each perforated on their lower side were filled with standardized horticultural earth. The seeds of weeds were sown into this earth, thenthe plastic dishes were placed in the greenhouse and, if necessary, sprinkled from above. The test plants were in the 2-4-leaf phase in the time of spraying. For spraying, the compounds were converted to aqueous mixtures by adding nonionic surface active additive in a known manner and the aqueous mixtures were applied onto the test plants by using a spraying equipment of DeVilbiss type. The plants treated were put on a perlite bed and a suitable moisture was ensured for the plants by sprinkling the perlite bed. The temperature in the greenhouse was maintained at 22°-24° C. in the day-time and at 18°-20° C. in the night; whereas the

EXAMPLE 16

Test of the post-emergent herbicidal activity

These experiments were arranged in the manner described in example 15. The doses of the compounds applied were further reduced. The results are given in Table 4.

EXAMPLE 17

Test of the post-emergent herbicidal effect

In this series of experiments the correlation between the optical activity and herbicidal effect of the compounds was investigated on monocotyledonous test plants. The experiments were arranged as described in Example 15. The results are summarized in Table 5.

The significations by letters and numbers are the same as described in Example 14.

TABLE 3

| Compound No. | Active ingred. kg/ha | Post-emergent herbicidal effect Herbicidal effect |||||||||||||||||||||||
|---|---|---|---|---|---|---|---|---|---|---|---|---|---|---|---|---|---|---|---|---|---|---|---|
| | | Monocotyledonous test plants |||||||||||Dicotyledonous test plants ||||||||||||
| | | Av | Ec | Sg | Ag | Al | Ap | Sh | Pm | Wh | Ri | Ma | Am | Ca | Sa | Ar | Ga | Mi | Sn | Pl | Sb | S | Sf | To | Af |
| 3 | 1.50 | 3 | 3 | 3 | 3 | 3 | 3 | 3 | 3 | 3 | 3 | 3 | 0 | 0 | 0 | 0 | 0 | 0 | 0 | 0 | 1 | 0 | 0 | 1 | 0 |
| 3 | 0.75 | 3 | 3 | 3 | 3 | 3 | 3 | 3 | 3 | 3 | 3 | 3 | 0 | 0 | 0 | 0 | 0 | 0 | 0 | 0 | 1 | 0 | 0 | 1 | 0 |
| 3 | 0.38 | 3 | 3 | 3 | 3 | 2 | 3 | 3 | 3 | 2 | 3 | 3 | 0 | 0 | 0 | 0 | 0 | 0 | 0 | 0 | 1 | 0 | 0 | 1 | 0 |
| 8 | 1.50 | 2 | 3 | 3 | 3 | 3 | 3 | 3 | 3 | 2 | 3 | 3 | 0 | 0 | 0 | 0 | 0 | 0 | 0 | 0 | 1 | 0 | 1 | 0 | 0 |
| 8 | 0.75 | 2 | 3 | 3 | 2 | 3 | 2 | 3 | 3 | 1 | 3 | 3 | 0 | 0 | 0 | 0 | 0 | 0 | 0 | 0 | 0 | 0 | 1 | 0 | 0 |
| 8 | 0.38 | 2 | 2 | 2 | 2 | 2 | 2 | 2 | 3 | 1 | 2 | 2 | 0 | 0 | 0 | 0 | 0 | 0 | 0 | 0 | 0 | 0 | 1 | 0 | 0 |
| 12 | 1.50 | 3 | 3 | 3 | 3 | 3 | 3 | 3 | 3 | 2 | 3 | 3 | 0 | 0 | 0 | 0 | 0 | 0 | 0 | 0 | 0 | 0 | 0 | 0 | 0 |
| 12 | 0.75 | 3 | 3 | 3 | 3 | 3 | 3 | 2 | 3 | 2 | 3 | 3 | 0 | 0 | 0 | 0 | 0 | 0 | 0 | 0 | 0 | 0 | 0 | 0 | 0 |
| 12 | 0.38 | 3 | 3 | 3 | 3 | 3 | 3 | 1 | 3 | 2 | 2 | 2 | 0 | 0 | 0 | 0 | 0 | 0 | 0 | 0 | 0 | 0 | 0 | 0 | 0 |
| 17 | 1.50 | 3 | 3 | 3 | 3 | 3 | 3 | 3 | 3 | 3 | 3 | 3 | 0 | 0 | 0 | 0 | 0 | 0 | 0 | 0 | 1 | 0 | 0 | 0 | 0 |
| 17 | 0.75 | 2 | 3 | 3 | 3 | 3 | 3 | 3 | 3 | 2 | 3 | 3 | 0 | 0 | 0 | 0 | 0 | 0 | 0 | 0 | 1 | 0 | 0 | 0 | 0 |
| 17 | 0.38 | 2 | 3 | 3 | 3 | 3 | 3 | 3 | 3 | 2 | 2 | 3 | 0 | 0 | 0 | 0 | 0 | 0 | 0 | 0 | 0 | 0 | 0 | 0 | 0 |
| 20 | 1.50 | 3 | 3 | 3 | 3 | 3 | 3 | 3 | 3 | 3 | 3 | 3 | 0 | 0 | 0 | 0 | 0 | 0 | 0 | 0 | 0 | 0 | 0 | 0 | 0 |
| 20 | 0.75 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 20 | 0.38 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 23 | 1.50 | 3 | 3 | 3 | 3 | 3 | 3 | 3 | 3 | 3 | 3 | 3 | 0 | 0 | 0 | 0 | 0 | 0 | 0 | 0 | 0 | 0 | 0 | 0 | 0 |
| 23 | 0.75 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 23 | 0.38 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 33 | 1.50 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 33 | 0.75 | 3 | 3 | 3 | 3 | 3 | 3 | 3 | 3 | 2.5 | 3 | 3 | 0 | 0 | 0 | 0 | 0 | 0 | 0 | 0 | 0 | 0 | 0 | 0 | 0 |
| 33 | 0.38 | 3 | 3 | 3 | 3 | 3 | 3 | 3 | 3 | 2 | 2.5 | 3 | 0 | 0 | 0 | 0 | 0 | 0 | 0 | 0 | 0 | 0 | 0 | 0 | 0 |
| 34 | 1.50 | 3 | 3 | 3 | 3 | 3 | 3 | 3 | 3 | 2.5 | 2.5 | 3 | 0 | 0 | 0 | 0 | 0 | 0 | 0 | 0 | 0 | 0 | 0 | 0 | 0 |
| 34 | 0.75 | 3 | 3 | 3 | 3 | 3 | 3 | 3 | 3 | 2 | 2.5 | 3 | 0 | 0 | 0 | 0 | 0 | 0 | 0 | 0 | 0 | 0 | 0 | 0 | 0 |
| 34 | 0.38 | 2.5 | 3 | 3 | 3 | 3 | 3 | 3 | 3 | 0.5 | 1.5 | 2 | 0 | 0 | 0 | 0 | 0 | 0 | 0 | 0 | 0 | 0 | 0 | 0 | 0 |
| 36 | 1.50 | 3 | 3 | 3 | 3 | 3 | 3 | 3 | 3 | 3 | 2.5 | 3 | 0 | 0 | 0 | 0 | 0 | 0 | 0 | 0 | 0 | 0 | 0 | 0 | 0 |
| 36 | 0.75 | 3 | 3 | 3 | 3 | 3 | 3 | 3 | 3 | 2.5 | 2.5 | 3 | 0 | 0 | 0 | 0 | 0 | 0 | 0 | 0 | 0 | 0 | 0 | 0 | 0 |

TABLE 3-continued

| Compound No. | Active ingred. kg/ha | Post-emergent herbicidal effect |||||||||||||||||||||||
|---|---|---|---|---|---|---|---|---|---|---|---|---|---|---|---|---|---|---|---|---|---|---|---|
| | | Herbicidal effect |||||||||||||||||||||||
| | | Monocotyledonous test plants ||||||||||| Dicotyledonous test plants ||||||||||||
| | | Av | Ec | Sg | Ag | Al | Ap | Sh | Pm | Wh | Ri | Ma | Am | Ca | Sa | Ar | Ga | Mi | Sn | Pl | Sb | S | Sf | To | Af |
| 36 | 0.38 | 2 | 3 | 3 | 2 | 3 | 2 | 2 | 3 | 2 | 2 | 3 | 0 | 0 | 0 | 0 | 0 | 0 | 0 | 0 | 0 | 0 | 0 | 0 | 0 |
| St. | 1.50 | 3 | 3 | 3 | 3 | 3 | 3 | 3 | 3 | 2 | 3 | 3 | 0 | 0 | 0 | 0 | 0 | 0 | 0 | 0 | 2 | 0 | 0 | 0 | 0 |
| St. | 0.75 | 3 | 3 | 3 | 3 | 3 | 3 | 3 | 3 | 2 | 3 | 3 | 0 | 0 | 0 | 0 | 0 | 0 | 0 | 0 | 1 | 0 | 0 | 0 | 0 |
| St. | 0.38 | 3 | 3 | 3 | 3 | 3 | 3 | 3 | 3 | 2 | 3 | 3 | 0 | 0 | 0 | 0 | 0 | 0 | 0 | 0 | 1 | 0 | 0 | 0 | 0 |

ST means the standardized control (which is the same as in Table 2)

TABLE 4

| Compound No. | Active ingred. kg/ha | Post-emergent herbicidal effect |||||||||
|---|---|---|---|---|---|---|---|---|---|---|
| | | Herbicidal effect |||||||||
| | | Av | Ec | Sg | Ag | Al | Ap | Pm | Dg | Bu | Ku |
| 2 | 0.4 | 2 | — | — | 2 | — | — | — | — | — | 2 |
| 2 | 0.2 | 1 | — | — | 2 | — | — | — | — | — | 2 |
| 2 | 0.1 | 0 | — | — | 1 | — | — | — | — | — | 2 |
| 2 | 0.05 | 0 | — | — | 0 | — | — | — | — | — | 1 |
| 3 | 0.4 | 3 | 3 | 3 | 3 | 3 | 3 | 3 | 3 | 2 | 3 |
| 3 | 0.2 | 3 | 3 | 3 | 3 | 3 | 3 | 3 | 2 | 2 | 3 |
| 3 | 0.1 | 2 | 3 | 3 | 2 | 3 | 3 | 3 | 2 | 2 | 2 |
| 3 | 0.05 | 2 | 2 | 3 | 2 | 2 | 2 | 3 | 2 | 1 | 2 |
| 17 | 0.4 | 3 | — | — | 3 | — | — | — | — | — | 2 |
| 17 | 0.2 | 2 | — | — | 2 | — | — | — | — | — | 2 |
| 17 | 0.1 | 1 | — | — | 1 | — | — | — | — | — | 2 |
| 17 | 0.05 | 0 | — | — | 1 | — | — | — | — | — | 1 |
| 20 | 0.4 | 3 | 3 | 3 | 3 | 2 | 3 | 3 | 2 | 2 | 3 |
| 20 | 0.2 | 2 | 3 | 3 | 2 | 2 | 3 | 2 | 2 | 1 | 2 |
| 20 | 0.1 | 2 | 2 | 3 | 2 | 2 | 2 | 3 | 2 | 1 | 2 |
| 20 | 0.05 | 1 | 1 | 2 | 1 | 2 | 1 | 2 | 1 | 1 | 1 |
| 21 | 0.4 | 3 | 3 | 3 | 3 | 3 | 3 | 3 | 3 | 2 | 3 |
| 21 | 0.2 | 3 | 3 | 3 | 3 | 2 | 3 | 3 | 2 | 2 | 3 |
| 21 | 0.1 | 1 | 2 | 3 | 2 | 2 | 2 | 3 | 2 | 1 | 2 |
| 21 | 0.05 | 1 | 1 | 3 | 1 | 1 | 1 | 3 | 1 | 1 | 2 |
| 23 | 0.4 | 3 | 3 | 3 | 3 | 3 | 3 | 3 | 3 | 2 | 3 |
| 23 | 0.2 | 2 | 3 | 3 | 3 | 3 | 3 | 3 | 3 | 2 | 3 |
| 23 | 0.1 | 2 | 3 | 3 | 2 | 2 | 3 | 2 | 2 | 2 | 2 |
| 23 | 0.05 | 2 | 3 | 3 | 2 | 2 | 3 | 2 | 2 | 2 | 2 |
| St. | 0.4 | 3 | — | — | 3 | — | — | — | — | — | 3 |
| St. | 0.2 | 2 | — | — | 2 | — | — | — | — | — | 2 |
| St. | 0.1 | 2 | — | — | 2 | — | — | — | — | — | 2 |
| St. | 0.05 | 2 | — | — | 1 | — | — | — | — | — | 2 |

St means the standardized control (see Table 2)—: not tested

TABLE 5

| Compound No. | Optical activity of the compound | Active ingred. kg/ha | Herbicidal effect ||||||||||||
|---|---|---|---|---|---|---|---|---|---|---|---|---|---|---|
| | | | Monocotyledonous test plants |||||||| Dicotyledonous test plants ||||
| | | | Ag | Al | Av | Dg | Ec | Pm | Sh | Ku | Am | Ca | Sz | Nf |
| 3 | (R)-(+) | 0.150 | 3 | 3 | 3 | 2.5 | 3 | 3 | 0.5 | 3 | 0 | 0 | 0 | 0 |
| 3 | (R)-(+) | 0.075 | 2.5 | 2.5 | 2.5 | 2.5 | 3 | 3 | 0.5 | 2.5 | 0 | 0 | 0 | 0 |
| 3 | (+)-(+) | 0.025 | 1 | 1 | 1 | 1 | 1 | 2.5 | 0.5 | 0.5 | 0 | 0 | 0 | 0 |
| 4 | (RS)-(±) | 0.150 | 2 | 2 | 3 | 2.5 | 3 | 3 | 0.5 | 3 | 0 | 0 | 0 | 0 |
| 4 | (RS)-(±) | 0.075 | 2 | 2 | 1.5 | 3 | 0 | 1 | 3 | 3 | 0 | 0 | 0 | 0 |
| 5 | (S)-(−) | 0.150 | 0 | 0 | 0 | 0 | 0 | 0 | 0 | 0 | 0 | 0 | 0 | 0 |
| 5 | (S)-(−) | 0.075 | 0 | 0 | 0 | 0 | 0 | 0 | 0 | 0 | 0 | 0 | 0 | 0 |
| 5 | (S)-(−) | 0.025 | 0 | 0 | 0 | 0 | 0 | 0 | 0 | 0 | 0 | 0 | 0 | 0 |
| 23 | (R)-(+) | 0.150 | 2.5 | 2.5 | 3 | 3 | 3 | 3 | 0.5 | 3 | 0 | 0 | 0 | 0 |
| 23 | (R)-(+) | 0.075 | 2 | 2 | 2 | 2.5 | 2.5 | 3 | 0 | 2 | 0 | 0 | 0 | 0 |
| 23 | (R)-(+) | 0.025 | 0.5 | 0 | 0 | 0 | 0 | 2.5 | 0 | 0 | 0 | 0 | 0 | 0 |
| 24 | (RS)-(±) | 0.150 | 2 | 2.5 | 3 | 1 | 2.5 | 3 | 2 | 2 | 0 | 0 | 0 | 0 |
| 24 | (RS)-(±) | 0.075 | 1.5 | 1 | 0 | 1 | 1.5 | 2.5 | 0 | 0.5 | 0 | 0 | 0 | 0 |
| 24 | (RS)-(±) | 0.025 | 0 | 0 | 0 | 0 | 1 | 0 | 0 | 0 | 0 | 0 | 0 | 0 |
| 25 | (S)-(−) | 0.150 | 0 | 0 | 0 | 0 | 0 | 0 | 0 | 0 | 0 | 0 | 0 | 0 |
| 25 | (S)-(−) | 0.075 | 0 | 0 | 0 | 0 | 0 | 0 | 0 | 0 | 0 | 0 | 0 | 0 |
| 25 | (S)-(−) | 0.025 | 0 | 0 | 0 | 0 | 0 | 0 | 0 | 0 | 0 | 0 | 0 | 0 |
| St. | (R)-(+) | 0.150 | 3 | 3 | 3 | 2.5 | 3 | 3 | 0.5 | 3 | 0 | 0 | 0 | 0 |
| St. | (R)-(+) | 0.075 | 2.5 | 3 | 3 | 2.5 | 3 | 3 | 0.5 | 3 | 0 | 0 | 0 | 0 |
| St. | (R)-(+) | 0.025 | 2 | 2 | 1 | 1 | 2 | 3 | 0.5 | 2 | 0 | 0 | 0 | 0 |
| St. | (RS)-(±) | 0.150 | 2.5 | 2.5 | 1.5 | 2 | 2 | 3 | 0.5 | 3 | 0 | 0 | 0 | 0 |
| St. | (RS)-(±) | 0.075 | 1.5 | 2 | 1.5 | 2 | 2 | 3 | 0.5 | 2 | 0 | 0 | 0 | 0 |
| St. | (RS)-(±) | 0.025 | 0 | 0 | 0 | 0 | 1 | 0 | 0.5 | 0 | 0 | 0 | 0 | 0 |

St means the standardized control, i.e. fluazifop, chemically n-butyl-2-[4-(5-trifluoromethyl-2-pyridyloxy)phenoxy]propionate

We claim:

1. An optically active compound selected from the group which consists of:
   N-allyl-2-{4-(5-trifluoromethyl-2-pyridyloxy)-phenoxy}-propionic acid amide;
   2'-(4-morpholino)ethyl 2-{4-(5-trifluoromethyl-2-pyridyloxy)phenoxy}propionate; and
   2-{4-(5-trifluoromethyl-2-pyridyloxy)phenoxy}-propionic acid (2-dimethyloxime) ethyl ester.

2. (R)-(+)-N-allyl-2-[4-(5-trifluoromethyl-2-pyridyloxy(phenoxy]-propionic acid amide as defined in claim 1.

3. A herbicidal composition, which comprises as active ingredient, a herbicidally effective amount of the compound defined in claim 1 in combination with a herbicidally acceptable inert carrier.

4. A selective herbicidal method of treatment against monocotyledonous weeds in the presence of both a monocotyledonous weed and a dicotyledonous plant, which comprises the step of preemergently or postemergently applying to a plant site having both the monocotyledonous weed and the dicotyledonous plant, an amount of the compound defined in claim 1 effective to selectively kill the monocotyledonous weed.

* * * * *